United States Patent
Reicher et al.

(10) Patent No.: US 10,510,449 B1
(45) Date of Patent: Dec. 17, 2019

(54) EXPERT OPINION CROWDSOURCING

(71) Applicant: MERGE HEALTHCARE SOLUTIONS INC., Hartland, WI (US)

(72) Inventors: Murray A. Reicher, Rancho Santa Fe, CA (US); Evan K. Fram, Paradise Valley, AZ (US)

(73) Assignee: MERGE HEALTHCARE SOLUTIONS INC., Hartland, WI (US)

( * ) Notice: Subject to any disclaimer, the term of this patent is extended or adjusted under 35 U.S.C. 154(b) by 866 days.

(21) Appl. No.: 14/196,885

(22) Filed: Mar. 4, 2014

Related U.S. Application Data

(60) Provisional application No. 61/780,640, filed on Mar. 13, 2013.

(51) Int. Cl.
- *G16H 15/00* (2018.01)
- *G16H 80/00* (2018.01)
- *G06F 19/00* (2018.01)

(52) U.S. Cl.
CPC ........... *G16H 80/00* (2018.01); *G06F 19/321* (2013.01); *G16H 15/00* (2018.01)

(58) Field of Classification Search
CPC ...... G06Q 50/22; G06Q 50/24; G06F 19/322; G06F 19/327
USPC ........................................................ 705/2, 3
See application file for complete search history.

(56) References Cited

U.S. PATENT DOCUMENTS

| | | | | |
|---|---|---|---|---|
| 6,669,482 B1 * | 12/2003 | Shile | ..................... | G09B 23/286 434/262 |
| 2002/0027901 A1 * | 3/2002 | Liu | ................... | H04M 3/42008 370/352 |
| 2002/0188475 A1 * | 12/2002 | Banta | .................... | G06F 19/321 705/3 |
| 2006/0059151 A1 * | 3/2006 | Martinez | ........... | G06F 17/30705 |
| 2006/0072797 A1 * | 4/2006 | Weiner | ................ | G06F 19/3487 382/128 |
| 2006/0200010 A1 | 9/2006 | Rosales | | |

(Continued)

OTHER PUBLICATIONS

Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.

(Continued)

*Primary Examiner* — Jason S Tiedeman
(74) *Attorney, Agent, or Firm* — Michael Best & Friedrich LLP

(57) ABSTRACT

An expert opinion crowdsourcing system is disclosed that may enable a person seeking an opinion (or other work product) to efficiently access experts (or other persons) who may provide such opinions (or other work products). For example, the system may enable a person to submit a request to the system, at which point the system may automatically match the request to one or more appropriate experts. The system may then provide the request to the appropriate experts, and receive opinions back from the experts in response to the request. The opinions may then be provided back to the person that submitted the request. The request may include various characteristics and/or criteria that may be matched to, or satisfied by, other characteristics or criteria associated with the experts. The system may include aspects whereby requests and/or opinions may be anonymized and/or combined.

10 Claims, 14 Drawing Sheets

(56) References Cited

U.S. PATENT DOCUMENTS

| | | | | |
|---|---|---|---|---|
| 2006/0241974 | A1* | 10/2006 | Chao | G06Q 10/00 |
| | | | | 705/2 |
| 2007/0288264 | A1* | 12/2007 | Brown | G06F 19/321 |
| | | | | 705/2 |
| 2008/0172446 | A1* | 7/2008 | Donovan | H04N 21/25875 |
| | | | | 709/202 |
| 2008/0243539 | A1* | 10/2008 | Barish | G06F 19/321 |
| | | | | 705/2 |
| 2009/0119258 | A1* | 5/2009 | Petty | G06Q 30/02 |
| 2009/0204436 | A1* | 8/2009 | Thorne | G06Q 10/06398 |
| | | | | 705/3 |
| 2009/0299766 | A1 | 12/2009 | Friedlander | |
| 2009/0319291 | A1* | 12/2009 | Noordvyk | G06F 19/3425 |
| | | | | 705/2 |
| 2010/0114603 | A1* | 5/2010 | Gutman | G06F 19/321 |
| | | | | 705/2 |
| 2010/0138230 | A1* | 6/2010 | Van Hoe | G06F 19/321 |
| | | | | 705/2 |
| 2010/0138239 | A1* | 6/2010 | Reicher | G06F 17/243 |
| | | | | 705/3 |
| 2010/0222649 | A1* | 9/2010 | Schoenberg | G06F 19/3418 |
| | | | | 600/301 |
| 2011/0276346 | A1* | 11/2011 | Reiner | G06F 19/327 |
| | | | | 705/3 |
| 2011/0282681 | A1* | 11/2011 | Gerlach | G06Q 10/107 |
| | | | | 705/2 |
| 2012/0010904 | A1* | 1/2012 | Buck | G06F 19/327 |
| | | | | 705/3 |
| 2012/0035944 | A1* | 2/2012 | Gobel | G06Q 10/10 |
| | | | | 705/2 |
| 2012/0123948 | A1 | 5/2012 | Fefer | |
| 2012/0245952 | A1* | 9/2012 | Halterman | G06F 19/3425 |
| | | | | 705/2 |
| 2012/0278097 | A1* | 11/2012 | Ghouri | G06Q 50/22 |
| | | | | 705/2 |
| 2013/0046551 | A1* | 2/2013 | Vahle | G06F 19/327 |
| | | | | 705/2 |
| 2013/0060576 | A1* | 3/2013 | Hamm | G06F 19/3418 |
| | | | | 705/2 |
| 2013/0094728 | A1* | 4/2013 | DeVries | G06F 19/321 |
| | | | | 382/128 |
| 2013/0110537 | A1* | 5/2013 | Smith | G06Q 10/06 |
| | | | | 705/2 |
| 2013/0144813 | A1 | 6/2013 | Sengupta | |
| 2013/0238647 | A1 | 9/2013 | Thompson | |
| 2013/0253940 | A1* | 9/2013 | Zziwa | G06Q 50/22 |
| | | | | 705/2 |
| 2014/0156645 | A1 | 6/2014 | Brust | |
| 2014/0201749 | A1 | 7/2014 | Bao | |
| 2015/0081364 | A1* | 3/2015 | Smith | G06Q 50/24 |
| | | | | 705/7.14 |

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Techolodies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions. Accessed on Feb. 9, 2015.

AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204.interWORKS%2ORISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 May 2014). © Carestream Health, Inc., 2014. Downloaded from http://www.carestream.com/csPACS_brochure_M1876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.

DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.

FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.

FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.

GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.

Handylife.com—Overview of Handy Patients Enterprise, in 2 page printout. Accessed from http://www.handylife.com/en/software/overview.html. Accessed on Feb. 18, 2015.

Handylife.com—Features of Handy Patients Enterprise, in 4 page printout. Accessed from http://www.handylife.com/en/software/features.html. Accessed on Feb. 18, 2015.

Handylife.com—Screenshots of Handy Patients Enterprise, in 2 page printout. Accessed from http://www.handylife.com/en/software/screenshots.html. Accessed on Feb. 18, 2015.

iCRco, I See the Future, in 12 pages, color brochure, (BRO80809AUS), © 2009 iCRco.ClarityPACS. Downloaded from http://www.claritypacs.com/pdfs/ISeeFuture_26_Web.pdf. Accessed on Feb. 9, 2015.

Imageanalysis, dynamika, 2 page color brochure. Downloaded from http://www.imageanalysis.org.uk/what-we-do. Accessed on Feb. 9, 2015.

(56) References Cited

OTHER PUBLICATIONS

Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx.com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
PHILIPS IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solution/Imaging/OfficePACSPowerDigitalImaging/index/hmt. Accessed on Feb. 9, 2015.
Stryker, OfficePACS Power—Digital Imaging, 8 page color brochure, (MPP-022 Rev 4 BC/MP 300 Jan. 2007). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/Solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Peer to Patent—Instructions for Using Peer to Patent, http://www.peertopatent.org/instuctions-for-using-peer-to-patent/, retrieved on Mar. 2, 2017 in 4 pages.
Peer to Patent, "First Pilot Final Result," Jun. 2012, http://www.peertopatent.org/wo-content/uploads/sites/2/2013/11/First-Pilot-Final-Results.pdf, downloaded Mar. 2, 2017 in 92 pages.

* cited by examiner

EXPERT OPINION CROWDSOURCING

CROSS-REFERENCE TO RELATED APPLICATION

This application claims the benefit of priority under 35 U.S.C. § 119(e) of U.S. Provisional Application No. 61/780,640, filed Mar. 13, 2013, the disclosure of which is hereby incorporated by reference herein in its entirety.

BACKGROUND

In medicine and other fields people may desire opinions from, or other work performed by, other persons, such as experts. For example, a patient or referring doctor may desire a medical opinion or evaluation by a specialist, another doctor, and/or any other type of expert. In another example, a person seeking legal counsel may desire an opinion from an expert such as an attorney.

SUMMARY

The systems, methods, and devices described herein each have several aspects, no single one of which is solely responsible for its desirable attributes. Without limiting the scope of this disclosure, several non-limiting features will now be described briefly.

According to an embodiment, a computer-implemented method is disclosed comprising: under direction of one or more hardware processors configured with specific software instructions, receiving a medical image series including one or more medical images; providing a user interface to a user, the user interface configured to allow the user to set preferences for selection of one or more reviewers, the preferences including rules indicating preferences regarding: whether reviewers offer availability to be contacted directly by the user; whether reviewers offer availability to review the medical image series as part of at least one of: a legal investigation, an insurance investigation, a consultation with a doctor, or a request of a patient; a minimum and/or maximum quantity of reviewers to be selected to review the medical image series; a minimum and/or maximum quantity of reviewers permitted to provide review information; and/or a minimum average user feedback required for reviewers to be selected for review of the medical image series; determining, based on the preferences set by the user, one or more reviewers to review the medical image series; and providing a notice to the determined one or more reviewers indicating availability of the medical image series for review.

According to another embodiment, a computing system is disclosed comprising: a storage device configured to store electronic software instructions; and one or more computer processors configured to execute the stored software instructions to cause the computing system to: receive a case including associated case characteristics, the case provided by a submitter, the case characteristics including a submitter type; receive expert information associated with experts, the expert information including expert characteristics associated with each respective expert, the expert characteristics including indications of accepted submitter types; match the case to one or more experts based on the case characteristics and the expert characteristics, wherein the submitter type associated with the case matches the indications of accepted submitter types associated with the one or more matched experts; and provide the case to the matched experts.

According to yet another embodiment, a computer-readable, non transitory storage medium is disclosed that stores computer-executable instructions that, when executed by a computer system, configure the computer system to perform operations comprising: receiving a case including associated case characteristics, the case provided by a submitter, the case characteristics including an indication that the submitter desires to be able to contact an expert; receiving expert information associated with experts, the expert information including expert characteristics associated with each respective expert, the expert characteristics including indications whether respective experts are willing to be contacted by the submitter; matching the case to one or more experts based on the case characteristics and the expert characteristics, wherein case characteristics associated with the one or more matched experts indicated that the respective experts are willing to be contacted by the submitter; and providing the case to the matched experts.

BRIEF DESCRIPTION OF THE DRAWINGS

The following aspects of the disclosure will become more readily appreciated as the same become better understood by reference to the following detailed description, when taken in conjunction with the accompanying drawings.

DETAILED DESCRIPTION

Overview

Figure 1A:
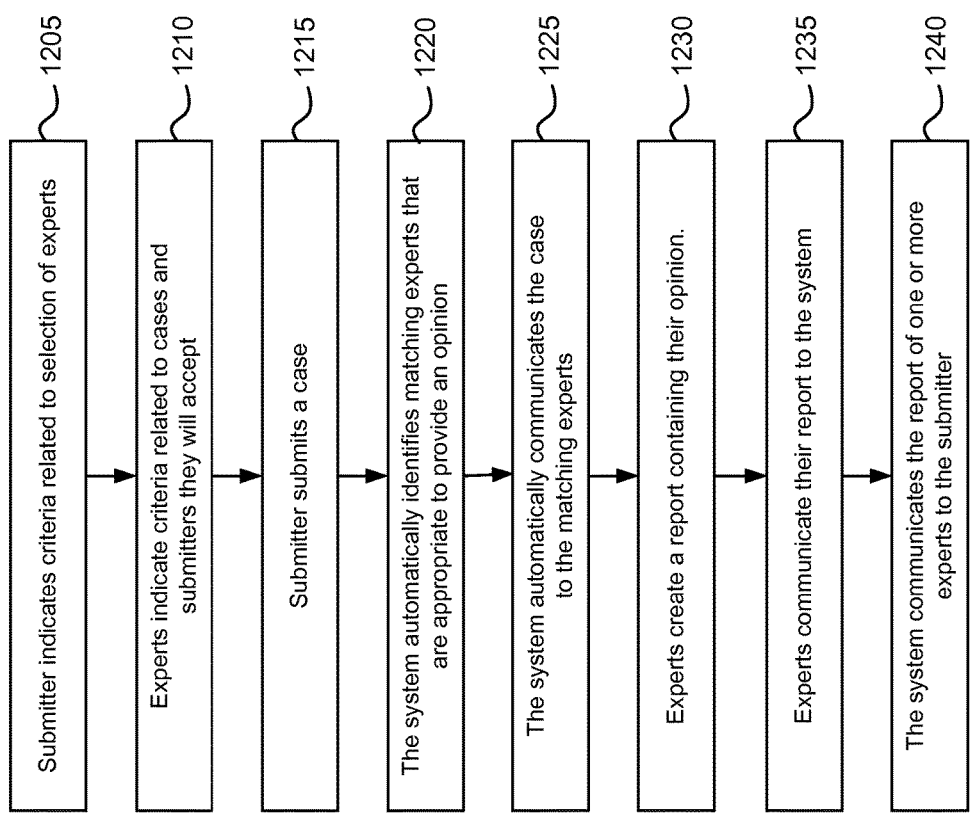
FIG. 1A is a flow diagram illustrating an example method of an expert opinion crowdsourcing system, according to an embodiment of the present disclosure.

As mentioned above, in medicine and other fields people may desire opinions from, or other work performed by, other persons. For example, a patient or referring doctor may desire a medical opinion or evaluation by a specialist, another doctor, and/or any other type of expert. In another example, a person seeking legal counsel may desire an opinion from an expert such as an attorney. As various persons desire or seek opinions, counsel, and/or other work from experts, there is a need for systems and methods that may allow such persons to efficiently access such experts.

Disclosed herein, according to various embodiments, is an expert opinion crowdsourcing system (also referred to as the "system") that may enable a person seeking an opinion (or other work product) to efficiently access experts (or other persons) who may provide such opinions (or other work products). For example, the system may enable a person to submit a request to the system, at which point the system may automatically match the request to one or more appropriate experts. The system may then provide the request to the appropriate experts, and receive opinions back from the experts in response to the request. The opinions may then be provided back to the person that submitted the request. In various embodiments, the request may include various characteristics and/or criteria that may be matched to, or satisfied by, other characteristics or criteria associated with the experts. Additionally, the system may include aspects whereby requests and/or opinions may be anonymized and/or combined, as described below. Further, according to various embodiments, experts and/or opinions provided by experts may be rated, as also described below. In some embodiments, a person submitting a request to the system may provide a payment to receive opinions.

While many of the examples and figures of the present disclosure describe the expert opinion crowdsourcing system in the context of medicine and medical image review and assessment, the systems and methods described have equal applicability to any number of other fields and, thus, references herein to such medical applications may be interpreted to cover any other field and/or applications.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Submitter: A person, group of persons, and/or any other type of entity, that may submit requests (for example, cases) to the expert opinion crowdsourcing system. For example, a submitter may be a doctor that submits a request for an evaluation of a medical image. In another example, a submitter may be a person that submits a request for an evaluation of a legal situation. In other examples, submitters may include patients, referring doctors, radiologists, insurance companies, attorneys that desire opinions from, or other work done by, experts such as radiologists or other legal professionals, and/or any other entity. Various characteristics may be associated with, or provided by, submitters which may be utilized by the system when matching requests (for example, cases) with experts, as described below. In various embodiments, characteristics may be referred to herein as "criteria" or "preferences."

Expert or Reviewer: A person, group of persons, and/or any other type of entity, that may receive requests from the expert opinion crowdsourcing system and provide responses to those requests. Various characteristics may be associated with (or provided by) experts or reviewers, which may be matched with criteria/characteristics associated with requests. For example, experts/reviewers may be associated with types, specialties and/or sub-specialties, medical image modalities, ratings, experience, and the like. In an example, an expert may be a radiologist (or other specialized doctor) that may receive requests to evaluate medical images, and may provide evaluations and/or opinions of those medical images. In another example, particular types of experts, for example radiologists, may be associated with a sub-specialty, for example, neuroradiology, musculoskeletal, and/or the like. In yet another example involving medical imaging, experts may include cardiologists and/or nuclear medicine specialists. In a further example, an expert/reviewer may be a lawyer that may receive a request for an evaluation of a legal situation, and may provide an evaluation or opinion regarding the legal situation. In various embodiments, experts/reviewers may specify particular characteristics related to their expertise, such as types of cases/requests that they are willing and/or unwilling to accept, and/or types of submitters from whom they are willing to accept cases, among others. For example, a doctor may indicate a specialty in evaluation of medical images of the brain, and/or that he accepts only requests to evaluate particular types of images of the brain (for example, MRI images). Although the term "expert" is used in the present disclosure, any type of person, group of persons, and/or any other type of entity that may receive requests for review of information and provide responses to the system may fall within the scope of the present disclosure (whether or not considered an "expert" under common usage of that term).

Case: A request provided by a submitter to the expert opinion crowdsourcing system. Cases may take any form, may be of any type, may include any characteristics and/or criteria, and may be from, or apply to, any field of endeavor. Characteristics associated with a case may include items that may be matched to, or satisfied by, other characteristics or criteria associated with experts. For example, a case may specify a role associated with the submitter (for example, patient, doctor or lawyer), request type (for example, medical image evaluation), an anatomical area of a medical image (for example, brain), a modality of a medical image (for example, PET, CT, MRI), a minimum rating associated with experts, and/or any other characteristic or criteria.

Report: A work product provided by an expert to the system (and/or submitter) in response to a received case. As with cases, reports may take any form, may be of any type, may include any characteristics and/or criteria, and may be from, or apply to, any field of endeavor. A report may be, for example, an evaluation, an opinion, a written product, a visual product, an audio product, a tactile product, a creative product, and/or any other work product. Although the term "report" is used in the present disclosure, any type of work product produced by an expert, in any medium, may fall within the scope of the present disclosure. In various embodiments, reports may be referred to herein as "reviews" and/or "review information."

Feedback: Quantitative and/or qualitative assessment of a report, such as an accuracy, quality, readability, format, etc. of a report. Feedback may also include an assessment of other characteristics of an expert that are not directly tied to the experts report, such as timeliness in providing the report, ease of availability of the expert, demeanor of the expert in dealing with the submitter, etc. Feedback, such as from a submitter that receives a report from an expert, may be used to score and/or rate the expert. Such ratings may then be used to filter the experts that are selected to review and report on a new case. For example, a submitter may restrict access to an uploaded case to only experts having a minimum feedback rating, where feedback ratings for experts are some aggregate (e.g., average, possibly in multiple feedback categories) of feedback ratings from multiple submitters. Other individuals or groups of individuals may provide feedback on reports and/or experts that provided respective reports. For example, "feedback entities," which is any entity that provides feedback on a report, may include experts, the submitter, and/or any other entity from which feedback on reports may be desired (e.g., individuals that are neither the submitter nor an expert that provides a report).

FIGURES

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

Example Method

FIG. 1A is a flow diagram illustrating an example method of an expert opinion crowdsourcing system (also referred to as the "system"), according to an embodiment of the present disclosure. The method of FIG. 1A may be performed by a crowdsourcing server 100 (FIG. 2A) and/or other suitable computing device. Depending on the implementation, the system may perform a method having more or fewer blocks than are shown, and/or the blocks may occur in a different order and/or in parallel in order to accomplish the methods and/or processes of the system.

Beginning at block 1205, a submitter may provide criteria and/or characteristics related to a case submission and/or a selection of experts (or other types of reviewers). In an embodiment, submitters may indicate criteria/characteristics related to how a case may be managed by the system. For example, as mentioned above, characteristics associated with a case may include items that may be matched to, or satisfied by, other characteristics or criteria associated with experts. For example, a case may specify a role associated with the submitter (for example, doctor or lawyer), request type (for example, medical image evaluation), an anatomical area of a medical image (for example, brain), a modality of a medical image (for example, PET, CT, MRI), a minimum rating associated with experts, and/or any other characteristic. Other examples of characteristics/criteria that may be provided by a submitter in association with a case may include:
  Qualifications for types of experts the submitter may be willing to accept. For example, a doctor with a particular specialty, or an expert having a particular rating.
  Requests for specific identified experts. For example, the submitter may provide a selection of particular experts from a list of available experts. In an embodiment, a list of available experts is provided by the system and may be automatically narrowed based on criteria/characteristics provided by the submitter (for example, characteristics mentioned above).
  A field or fields of expertise, and/or a triage function. For example, the submitter may direct a case to an expert with a particular specialty, for example, neuroradiology, musculoskeletal, GI, cardiology, or the like.
  A number of expert reports and/or opinions desired. For example, the submitter may desire 1, 2, 3, 4, 5, and/or more opinions. In an example, the submitter may desire reports from multiple different experts having different characteristics.
  A request that a case be provided to experts who are willing to verbally discuss the case. In an embodiment, such a request provided to the system may require an additional charge to, or payment by, the submitter.
  An expert blacklist. For example, a submitter may blacklist, or indicate that they do not want a case to be matched with, experts with whom they may have had an unsatisfactory interaction in the past. In another example, a submitter may indicate that experts having a rating below a particular threshold are to be blacklisted.
  A request that the case be provided to an expert who is available and/or able to complete a report in a particular period of time, or in a particular timeframe. As mentioned below, experts may provide, and/or the system may automatically determine, an availability and/or an expected time to complete a report for any particular expert. Accordingly, in an embodiment, a submitter may indicate a desire and/or requirement that a report be completed within a particular period of time, and the system may match the case to experts that are available and/or capable (and/or likely) to complete the report in the particular period of time.

Moving to block 1210, experts may indicate and/or be associated with criteria and/or characteristics related to cases and/or submitters they will accept. For example, experts may indicate criteria/characteristics related to how the system matches them with cases and submitters. As mentioned above, experts may be associated with types, specialties and/or sub-specialties, medical image modalities, ratings, and the like. Other examples of characteristics/criteria that may be provided by, and/or be associated with, experts may include:
  Specific types of exams or other work the experts are willing to take, for example, MRI and CT of the elbow.
  Rules indicating types of submitters from which the experts may accept cases and/or purposes of the requested expert review for which the experts may accept cases. For example, an expert may indicate that they may (or may not) accept cases based on one or more of the following rules/criteria:
    Cases from patients who want to discuss results with the expert.
    Cases from patients who do not require a discussion.
    Whether or not the case is from a referring doctor and/or a type of doctor. For example, an expert may indicate "willing to consult on elbow MRI scans with orthopedic surgeons but not with family practice doctor."
    Legal cases where the submitter is an attorney working for a defendant.
    Legal cases where the submitter is an attorney working for a plaintiff.
    Cases submitted by insurance companies.
  A blacklist of particular submitters. For example, an expert may blacklist a submitter (or group of submitters) with whom the expert has had an unsatisfactory interaction in the past. In an embodiment, submitters that are blacklisted by an expert may not see the expert on a list of available experts, and/or the system may not select the expert for review of cases from submitters that are blacklisted by the particular expert (even if, for example, the expert matches other criteria established by the submitter).

An indication of a schedule or availability. For example, an expert may provide and manage a schedule of their availability with the system such that they may not be matched to cases that they may be unavailable to accomplish. In an embodiment, the system may automatically determine an availability of an expert based on past availability, past performance, a current case load, and/or other characteristics of the expert.

An indication of an expected time to complete a report. For example, an expert may provide, and/or the system may automatically determine (based on, for example, past performance, a current case load, and/or other characteristics of the expert), an indication of an expected amount of time to complete a report for a case. In an embodiment, multiple expected times to complete various types of report may be provided for a particular expert.

In an embodiment, and as described below in reference to FIG. 1B, the system may enable an expert to view particular cases (for example, cases with which they are matched) such that the expert may evaluate the case and decide whether or not to accept it.

At block 1215, a submitter may submit a case to the system. For example, the system may provide a user interface and/or computing device (as described below in reference to FIGS. 2A-2B) through which the submitter may provide a case, including various files, images, information, characteristics, and/or the like. Examples of case submissions are described below in reference to FIGS. 4-8. In an embodiment, block 1205 is performed in conjunction with block 1215 such that criteria for selection of experts is associated with the current case being submitted. Some submitters may have different criteria for each case submission and, thus, may provide those criteria along with the case submission.

At block 1220, the system may match a submitted case with particular experts. For example, the system may automatically identify experts having characteristics appropriate to provide an opinion, report, or review on the submitted case. In an embodiment, matching experts may be those having all characteristics identified in the submitted case. In another embodiment, matching experts may be those having most, or particular, characteristics identified in the submitted case. In an embodiment, in the event where no experts match the submitted case, the submitter may be provided with the option of altering the characteristics associated with the case so as to target, for example, a greater breadth of experts. In various embodiments, the system may include rules and/or a rules engine that may perform matching of cases to experts.

At block 1225, the system may communicate the case to matching experts. In an embodiment, communication of the case may be performed automatically once particular experts have been identified as having characteristics matching the case. In various embodiments, a case may be provided to one or many experts.

At block 1230, the experts that received the case may create reports/reviews in accordance with the case information and/or specifications. In an example, the experts may create reports including opinions of a medical image. As mentioned above, a report produced by an expert may take any form (for example, written or verbal), and may be provided via any medium.

At block 1235, the experts may provide their reports to the system. An expert may, in an embodiment, communicate their report to the system through a user interface and/or computing device, as described below in reference to FIGS. 2A-2B.

At block 1240, the system may communicate the reports provided by the one or more experts to the submitter. In an embodiment, and as described below in reference to FIGS. 2A-2B, the reports may be communicated to the submitter through a user interface and/or computing device. In an embodiment, the submitter may evaluate various reports and select a preferred report. In another embodiment, the system may select a particular report and provide that report to the submitter. For example, the system may evaluate the reports according to a set of rules and/or criteria to determine a quality of the reports. Accordingly, the system may provide a report, or reports, to the submitter that meet a quality threshold. In an embodiment, the submitter may provide feedback to the system based on the quality of the reports. Such feedback may, for example, be used by the system to score and/or rate the various experts from whom reports were received.

Figure 1B:
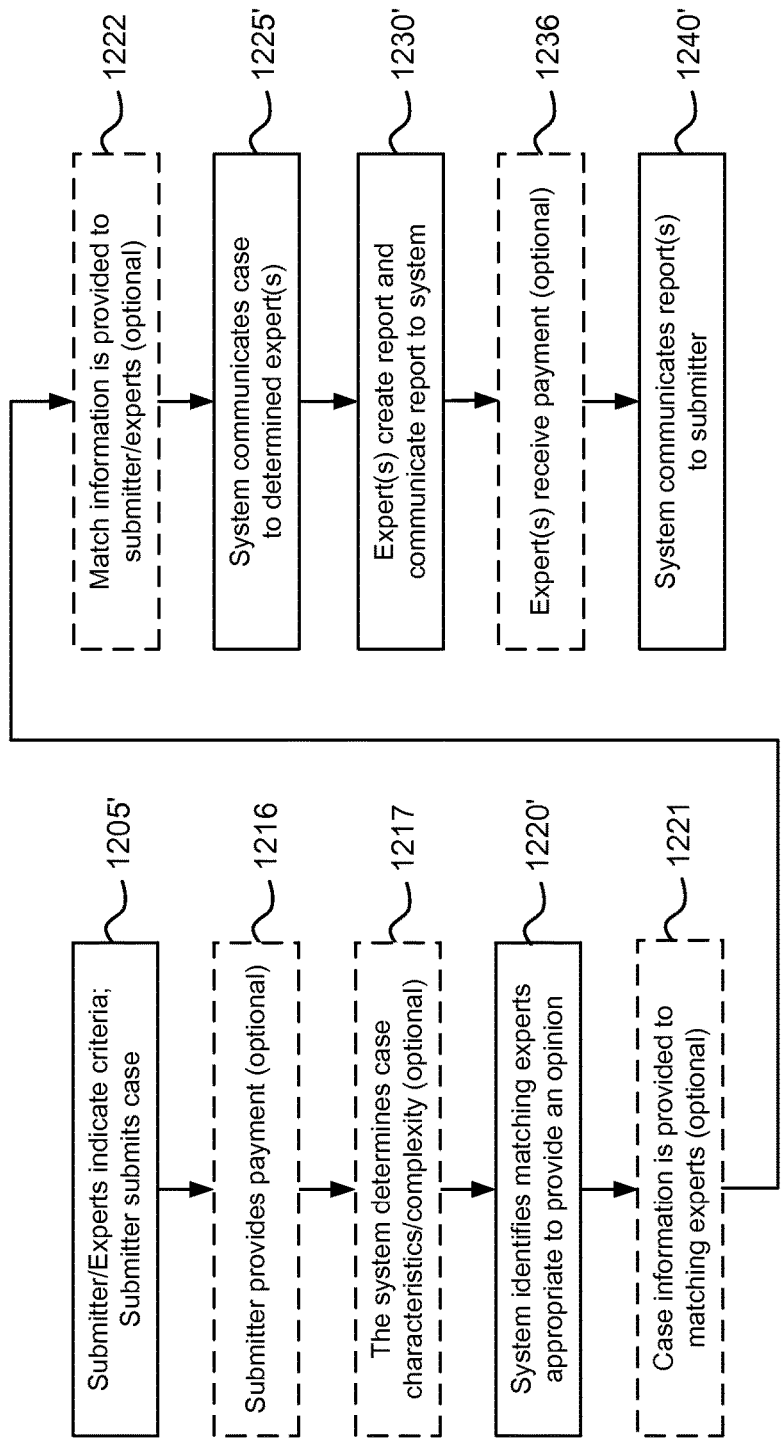
FIG. 1B is a flow diagram illustrating another example method of an expert opinion crowdsourcing system similar to the method of FIG. 1A, according to an embodiment of the present disclosure.

FIG. 1B is a flow diagram illustrating another example method of an expert opinion crowdsourcing system similar to the method of FIG. 1A, but including additional optional blocks, according to an embodiment of the present disclosure. As with FIG. 1A, the method of FIG. 1B may be performed by the crowdsourcing server 100 (FIG. 2A) and/or other suitable computing device. Depending on the implementation, the system may perform a method having more or fewer blocks than are shown, and/or the blocks may occur in a different order and/or in parallel in order to accomplish the methods and/or processes of the system.

At block 1205' (where the prime indicator (') in the reference number indicates a block or a variation of a block (e.g., a combination of multiple blocks in a previous figure) having the same reference number in a previous figure (e.g., FIG. 1A)), a submitter and one or more experts may provide and/or indicate various criteria and/or characteristics that may be used in matching a case of the submitter to one or more experts. The operation of this block is similar to the operation of blocks 1205 and 1210 described above in reference to FIG. 1A. Additionally, at block 1205' the submitter may submit a case to the system. This operation is similar to the operation of block 1215 described above in reference to FIG. 1A. Accordingly, the description provided above with reference to blocks 1205, 1210, and/or 1215 may be applied to the present block 1205'.

In an embodiment, at optional block 1216, the submitter may provide a payment along with submission of the case. Alternatively, the submitter may provide a payment after receipt of a report (for example, after block 1240' described below). The payment, or a portion of the payment, provided by the submitter may, as described below, be provided as a compensation to one or more experts who are matched and/or provide a report to the system and/or the submitter. In an embodiment, a portion of the payment provided by the submitter may be provided to the system as a compensation for the use of the system.

At optional block 1217 the system may determine various characteristics, a complexity, and/or other information associated with the case. The characteristics, complexity, and/or other information may be determined from, for example, information provided by the submitter, metadata associated with the case and/or one or more items of information extracted from the case (for example, from headers, header files, metadata files or metafiles, notes or other textual content, image recognition, and/or the like). According to one embodiment, the system may determine the various characteristics/complexity automatically. In an embodiment, the determined characteristics and/or complexity may be used by the system in addition to the characteristics/criteria provided by the submitter for selection of experts (as further described below).

In an embodiment, as described above, criteria for selection of experts may be associated with a current case being submitted. Some submitters may have different criteria for each case submission and, thus, may provide those criteria along with the case submission. Additionally, in an embodiment blocks 1205' and 1217 may be performed together such that automatically determined characteristics and submitter provided characteristics associated with the case may be provided along with the case submission.

At block 1220', the system may match a submitted case with particular experts. For example, as described above, the system may automatically identify experts having characteristics appropriate to provide an opinion or report on the submitted case. The operation of this block is similar to the operation of block 1220 described above in reference to FIG. 1A. Accordingly, the description provided above may be applied to the present block.

At optional block 1221, case information may be provided to matching experts. For example, various items of information and/or characteristics associated with the case may be provided to a matching expert such that the expert may determine whether the expert wants to, is able to, and/or is qualified to create a report and/or evaluate the case. For example, an expert may want to not only see a list of submitted cases (or exams), but the attributes of the case that were extracted from metafiles, reports, and/or other records associated with the case. In this embodiment, an expert may be enabled to decide if he or she wants to tackle the case compared to other listed cases.

At optional block 1222, match information may be provided to the submitter and/or the expert(s). For example, the system may provide information to one or more submitters and/or experts regarding a closeness (or strength) of a match (or a correlation) between a case and a particular expert(s). For example, the system may determine that Expert A is a 70% match with a particular submitted case, while Expert B is an 80% match with the same case. The closeness of a match (for example, the percentages used in the previous example), may be determined based on, for example, a number of characteristics common between the case and the expert. Match information may also be reported in the form of a list of matching characteristics between the expert and the case and/or qualifications of matched experts, among others. In another example, match information may include a list of matched experts ordered according to a particular ranking. Experts may be ranked according to a closeness of a match, an experience, a rating, and/or associated qualification, just to name a few.

Such match information may be provided to the expert(s) such that the expert(s) may make a determination regarding whether they desire and/or feel qualified to take the case (for example, relative to more qualified experts). Such match information may also be provided to the submitter such that the submitter may make a determination regarding selection of a particular expert based on the closeness of the match. In an example, when multiple experts are matched with a case (and/or accept a match after reviewing information associated with the case), the submitter may desire to see how the experts rank in terms of the experts' attributes matching with extracted characteristics from the case. For example, the submitter of a medical image for evaluation may want to see that there are three general radiologists who seek to render an opinion, one junior neuroradiologist, and one senior neuroradiologist with spectroscopy expertise. The methods described above may similarly be applied in the matching of other types of experts including, for example, legal, ethical, and the like. As mentioned below, the system may determine prices for reports from particular experts based on matching information and/or any other characteristics or criteria mentioned above. Such price information may also be useable by the submitter to select a particular expert or particular experts.

At block 1225', the system may communicate the case to one or more determined experts. In an embodiment, communication of the case may be performed automatically once particular experts have been determined based on, for example, expert characteristics matching case characteristics and/or selections/determinations made by the submitter based on provided case and/or match information, as described above. In various embodiments, a case may be provided to one or many experts. Aspects of the operation of this block are similar to the operation of block 1225 described above in reference to FIG. 1A. Accordingly, the description provided above may be applied to the present block.

At block 1230', the experts that received the case may create reports in accordance with the case information and/or specifications, and the experts may communicate the reports to the system. The operation of this block is similar to the operation of blocks 1230 and 1235 described above in reference to FIG. 1A. Accordingly, the description provided above may be applied to the present block.

At optional block 1236, the experts that have provided their report to the system may receive payment or compensation, as mentioned above. Alternatively, the experts may receive payment after their report is selected and/or accepted by the submitter. In various embodiments, the system may automatically determine prices associated with expert reports. Prices may be determined based on, for example, a complexity of a case, a degree of matching between an expert and a case, an expert's experience and qualifications, and/or an expert's matching rank among other matching experts, among others. In other embodiments, the submitter may provide a compensation amount per report or for a group of reports. For example, a submitter may offer $15 per report, or possibly $15 for each report (up to a maximum of 3) from a reviewer with a particular qualification, and compensation of $30 (for only a single reviewer) for a review with a different (e.g., more specialized) experience. In one embodiment, the experts may set a minimum compensation that they will accept for review of a case (possibly having different minimums for different case types/characteristics), or may bid on review of cases such that a lowest bidding reviewer wins the right to be compensated for review of a case.

At block 1240', the system may communicate the reports provided by the one or more experts to the submitter. The operation of this block is similar to the operation of block 1240 described above in reference to FIG. 1A. Accordingly, the description provided above may be applied to the present block.

In various embodiments, the system may include various other aspects and/or features including, for example:
The system may provide tools that facilitate reading of cases, such as within a browser wherein reviewers access case information. For example, the system may include specialized functionality that allows, for example, radiologists to efficiently view and interpret medical images, such as those that exist within Picture Archive and Communication Systems (PACS).

The system may interface with, or be integrated into, Personal Health Record systems (PHR) such that patients may make requests directly from within a PHR and/or reports from experts may be communicated to a PHR.

The system may interface with, or be integrated into, an Electronic Medical Record system (EMR), Personal Health Record systems (PHR), or Picture Archive and Communication System (PACS) to allow unidirectional or bidirectional communication of cases and/or reports managed by the expert opinion crowdsourcing system.

The expert opinion crowdsourcing system may be linked to other systems that experts may use for interpreting cases (for example, to facilitate in the interpretation of cases). For example, the system may be interfaced with a PACS system so that a radiologist, serving as an expert, may utilize the PACS system to interpret a case such as a medical imaging exam.

The system may require that submitters include contact information for a patient's physician in the event that the expert finds an important, but previously undiagnosed, condition (for example, a cerebral aneurysm).

As mentioned above, in various embodiments, the system may perform processes of rating experts. Ratings may be provided by, for example, submitters, other experts, and/or rules/criteria of the system. In some embodiments, ratings may be used, as mentioned above, as criteria for matching submitters, experts, and cases. Ratings of experts may be determined in a number of ways. For example, expert ratings may be based on training, input from submitters, input from other experts, testing (for example, using known test cases), similarities of the expert's reports with reports of other experts, follow-up with patients, comparison of the expert's prior reports with clinical or pathological follow-up, and/or the like.

In various embodiments, aggregate rating values may be visible to submitters to select from a list of available experts and/or aggregate ratings may be used as criteria for automated selection of experts (for example, a submitter may indicate that experts have minimum rating of 4 for the submitter's case). In an embodiment, the system may automatically stop sending cases to experts with ratings that fall below a particular level or threshold.

Example Implementation Systems and Devices

Figure 2A:
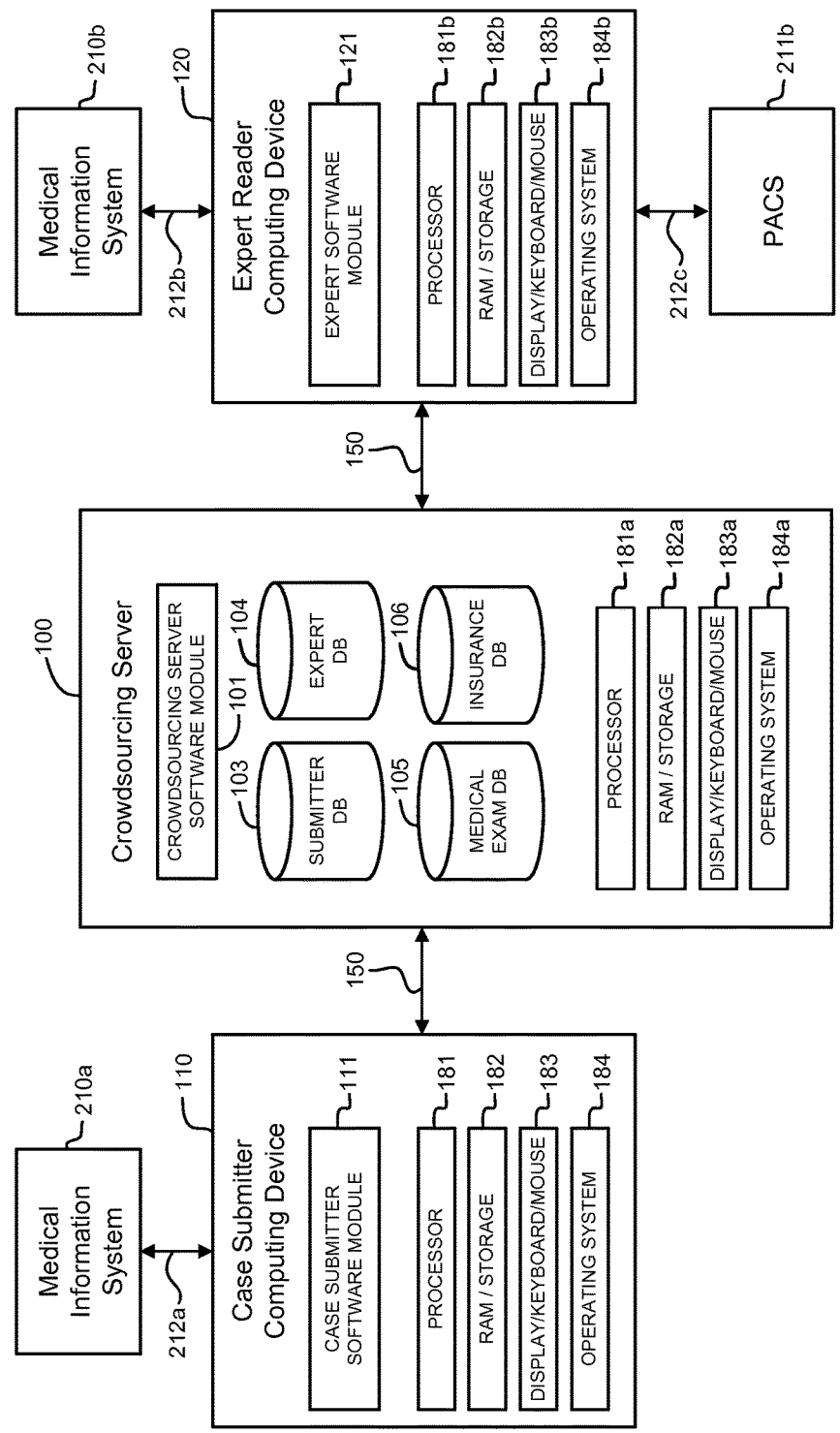
FIGS. 2A-2B are block diagrams illustrating example computing systems and/or devices that may be included in the expert opinion crowdsourcing system, according to embodiments of the present disclosure.
Figure 2B:
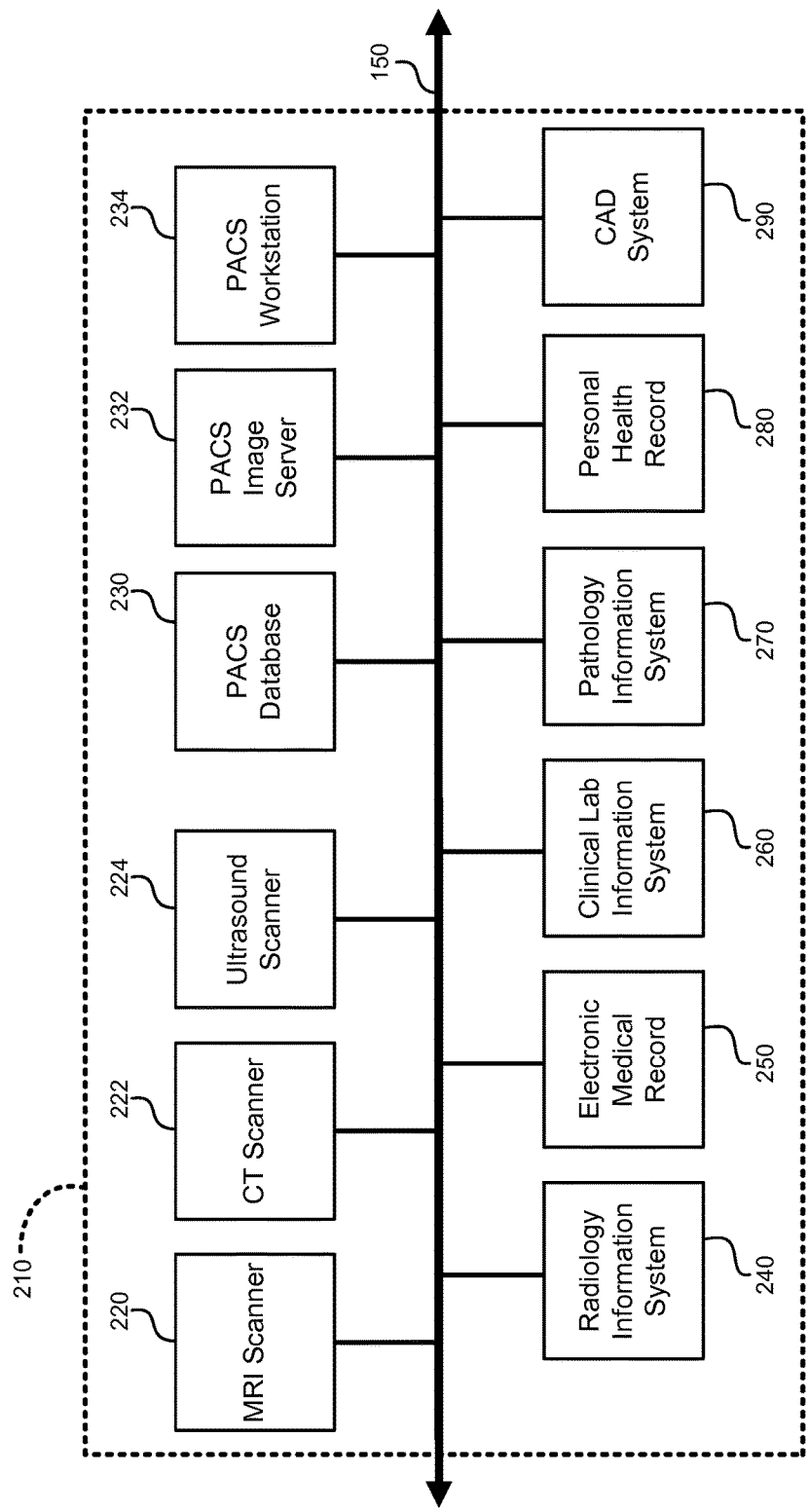

FIGS. 2A-2B are block diagrams illustrating example computing systems and/or devices that may be included in the expert opinion crowdsourcing system, according to embodiments of the present disclosure. Referring to FIG. 2A, the block diagram shows that the system may include a Case Submitter Computing Device 110, a Crowdsourcing Server 100, and an Expert Reader Computing Device 120. Further, the system may optionally include, in some embodiments, a Medical Information System 210a, a Medical Information System 210b, and/or a Picture Archive and Communication System (PACS) 211b. Each of the components of the system may be in communication with any other component via, for example, wired and/or wireless data connections. For example, medical information systems 210a and 210b, and PACS 211b, may be in communication with case submitter computing device 110 and/or expert reader computing device 120 via communication links 212a, 212b, and/or 212c. Similarly, case submitter computing device 110, crowdsourcing server 100, and/or expert reader computing device 120 may be in communication with one another via, for example, communication links 150. In various embodiments, the system may include more or fewer components than are shown in FIG. 2A. Such communication links (for example, links 212a, 212b, 212c, and 150) may include one or more wired and/or wireless communication networks, such as local area networks, wide area networks, cellular networks, the Internet, and the like.

In the example of FIG. 2A, the case submitter computing device 110 may include a case submitter software module 111, a processor 181, a random access memory (RAM) and/or storage 182, input/output devices 183 (including, for example, a display, keyboard, and/or mouse), and/or an operating system 184. The case submitter computing device 110 may be used by a submitter to communicate a case and/or case information, for example, a medical case including medical information and/or various medical data (for example, medical images, reports, records, and the like), to the crowdsourcing server 100. In an embodiment, the case submitter software module 111 may, as described below, include computer-executable instructions, or other software logic, that may be executed by, for example, the processor 181 to cause the case submitter computing device 110 to, for example: receive and/or determine characteristics associated with a submitter and/or case, provide submitter and case information (including characteristics) to the crowdsourcing server 100, receive report information from the crowdsourcing server 100, provide a user interface through which a submitter may provide case information, and/or the like. In various embodiments, the case submitter software module 111 may include instructions, or other software logic, to implement any other aspect or functionality of the system, as described herein. Provided case information may be transmitted, by the case submitter computing device 110, to the crowdsourcing server 100.

In various embodiments, case submitter computing device 110 may or may not communicate with other systems, such as medical information system 210a and/or a Personal Health Care Record (PHR) system, a Picture Archive and Communication System (PACS), and/or an Electronic Medical Record (EMR) system. In some embodiments the functionality required to submit cases to crowdsourcing server 100 may be integrated into other systems, such as a PACS, PHR or EMR, for example by incorporating case submitter software module 111 into these other systems. For example, in some embodiments the functionality discussed with reference to the case submitter computing device 110, including the case submitter software module 111, may be included in another computing device, such as an online PHR system that allows members to submit cases for review by selecting experts via the crowdsourcing server 100.

Crowdsourcing server 100 may include a crowdsourcing server software module 101, a processor 181a (similar to the processor 181), a random access memory (RAM) and/or storage 182a (similar to the RAM/storage 182), input/output devices 183a (similar to input/output devices 183), an operating system 184a (similar to operating system 184), and/or various databases including, for example, a submitter database 103, an expert database 104, a medical exam database 105, and/or an insurance database 106. Similar to the case submitter software module 111 described above, in an embodiment, the crowdsourcing server software module 101 may, as described below, include computer-executable instructions, or other software logic, that may be executed by, for example, the processor 181a to cause the crowdsourcing server 100 to, for example: receive case information from submitters, receive expert information from experts, match cases to experts, provide cases to experts, receive reports from experts, provide reports to submitters, rate experts, and/or the like. In various embodiments, the crowdsourcing server software module 101 may include instructions, or other software logic, to implement any other aspect or functionality of the system, as described herein. Crowdsourcing server 100 may communicate with case submitter computing device 110 and/or expert reader computing device 120 using any one or combination of wired and/or wireless communication techniques, such as local area networks, wide area networks, cellular networks, the Internet, email, and the like.

In various embodiments, the crowdsourcing server 100 may include or communicate with one or more databases or data structures. For example, submitter database (DB) 103 may hold information related to submitters, and expert DB 104 may hold information related to experts. Medical exam DB 105 may hold information related to cases submitted. In some embodiments, medical exam DB 105 may hold information related to reports of experts related to the submitted cases. Insurance DB 106 may hold information related to characteristics of medical insurance policies. For example, insurance DB 106 may including information related to whether or not an expert may charge a submitter for rendering an opinion on a submitted case. In other embodiments, insurance DB 106 may include information on specific medical insurance covering patients associated with submitted cases. In other embodiments, insurance DB 106 may include insurance policies for which experts are contracted.

In various embodiments the various types of information described above may reside in databases other than the ones described. Additionally, the databases illustrated with reference to crowdsourcing server 100 may comprise any other type of data structure for storing and/or organizing data, including, but not limited to, relational databases (for example, Oracle database, mySQL database, and the like), spreadsheets, XML files, and text files, among others. The various terms "database," "data store," and "data source" may be used interchangeably in the present disclosure. Further, in various embodiments the databases illustrated with reference to crowdsourcing server 100 may be remotely located such that, for example, the crowdsourcing server 100 may accesses such data structures via one or more networks.

Expert reader computing device 120 may include an expert software module 121, a processor 181*b* (similar to the processor 181), a random access memory (RAM) and/or storage 182*b* (similar to the RAM/storage 182), input/output devices 183*b* (similar to input/output devices 183), and/or an operating system 184*b* (similar to operating system 184). The expert reader computing device 120 may be used by an expert, in various embodiments described herein, to receive case information and/or provide reports, among other things. For example the expert reader computing device 120 may communicate with crowdsourcing server 100 to provide the expert access to cases. In some embodiments it may be used by the expert to view a case and/or create a report of his opinion. Similar to the case submitter software module 111 described above, in an embodiment, the expert software module 121 may, as described below, include computer-executable instructions, or other software logic, that may be executed by, for example, the processor 181*b* to cause the expert reader computing device 120 to, for example: receive and/or determine characteristics associated with an expert, provide expert information (including expert characteristics) to the crowdsourcing server 100, receive case information from the crowdsourcing server 100, provide a user interface through which an expert may view case information, provide case information to an expert or other computing device, receive from and/or produce reports for experts, provide reports to the crowdsourcing server 100, and/or the like. In various embodiments, the expert software module 121 may include instructions, or other software logic, to implement any other aspect or functionality of the system, as described herein.

In various embodiments, the expert reader computing device 120 may communicate with other systems, for example medical information system 210*b* and/or a PHR system, a PACS (such as PACS 211*b*), and/or an EHR system. For example, a case communicated to expert reading computing device 120 may be communicated to PACS 211*b* so that a radiologist expert may efficiently interpret a case and render an opinion in the form of a report. In some embodiments the functionality of expert reader computing device 120 may be integrated into other systems or components, such as a PACS, PHR, and/or EHR. For example, in some embodiments the expert software module 121 may be incorporated into one or more of these other components.

Referring to FIG. 2B, the block diagram illustrates examples of components that may be present in a Medical Information System, such as either of the optional medical information systems 210*a* or 210*b* of FIG. 2A. In various embodiments, a medical information system may include one or more of the components illustrated, or other systems related to the management of medical information. Various devices and subsystems illustrated in FIG. 2B may be connected to a network or various devices of the system (for example, via network 150 and/or communication links 212*a*, 212*b*, and/or 212*c*) and may be in communication with one or more of the components illustrated in FIG. 2A (for example, case submitter computing device 110, crowdsourcing server 100, and/or expert reader computing device 120).

The medical information system 210 of FIG. 2B may include an MRI scanner 220, a CT scanner 222, an Ultrasound scanner 224, a PACS database 230, a PACS image server 232, a PACS workstation 234, a radiology information system 240, an electronic medical record system 250, a clinical lab information system 260, a pathology information system 270, a personal health record 280, and/or a CAD system 290, among other components. The MRI scanner 220 (among the other types of scanners), which may be used to acquire MRI images from patients, may share the acquired images with other devices on the network 150. The network 150 may also be in communication with one or more CT scanners 222 and/or ultrasound scanners 224. The CT scanners 222 and Ultrasound scanners 224 may also be used to acquire images and, like the MRI scanner 220, may store acquired images and/or share acquired images with other devices via the network 150. Any other scanner or device capable of inputting or generating information that may be presented to a user (such as a submitter or expert) as images, graphics, text, and/or sound may be included in the medical information system 210. Examples of other types of devices may include angiography, nuclear medicine, radiography, endoscopy, pathology, dermatology, and/or the like.

Also connected to the network 150 may be the Picture Archiving and Communications System (PACS) Database 230, PACS Image Server 232, and PACS workstation 234. PACS systems may be used for storage, retrieval, distribution, and presentation of images (such as those created and/or generated by the MRI scanner 220, CT Scanner 222, and/or Ultrasound Scanner 224). Medical images may be stored in an independent format, an open source format, and/or some other proprietary format. For example, images may be stored in the PACS system in a Digital Imaging and Communications in Medicine (DICOM) format. The stored images may be transmitted digitally via the PACS system, which may reduce or eliminate the need for manually creating, filing, and/or transporting film and film jackets.

The network 150 may also be connected to the radiology information system (RIS) 240. The radiology information system 240 may be a computerized data storage system that may be used by radiology departments to store, manipulate, and/or distribute patient radiological information.

Also attached to the network 150 may be the electronic medical record (EMR) system 250. The EMR system 250 may be configured to store and make accessible to a plurality of medical practitioners computerized medical records. Also attached to the network 150 may be the clinical laboratory information system 260. Clinical laboratory information system 260 may be a software system which stores information created or generated by clinical laboratories. Also attached to the network 150 may be the digital pathology system 270, which may be used to digitally manage and store information related to medical pathology.

As shown in the embodiment of FIG. 2B, the personal health record (PHR) system 280 may also be coupled to the network. The PHR system 280 may be configurable by a particular patient in order to manage health records and data associated with the patient (and/or the patient's family or others in the care of the patient). Also attached to the network 150 may be the computer aided diagnosis system (CAD) 290 used to analyze images using one or more computer aided techniques.

Other systems, devices, and/or components may also be in communication via the network 150. Such other systems, devices, and/or components may include, for example, a 3D Processing System used to perform computations on imaging information to create new views of the information (for example, 3D volumetric display, Multiplanar Reconstruction (MPR), and Maximum Intensity Projection reconstruction (MIP)).

In various embodiments, other computing devices that store, provide, acquire, and/or otherwise manipulate medical data may also be coupled to the network 150 and may be in communication with one or more of the devices illustrated in the figures.

Example Communications Among Submitters and Experts

Figure 3:
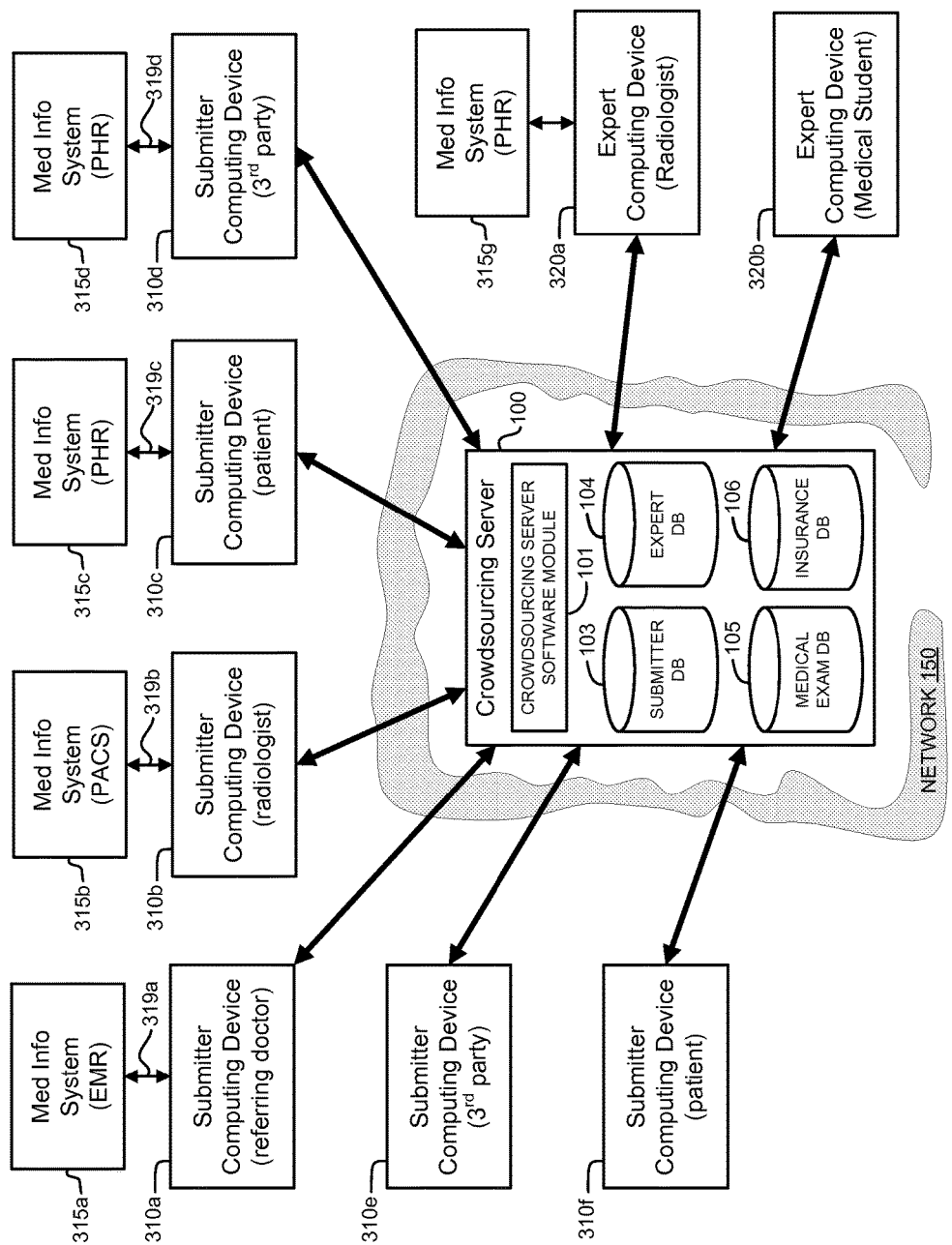
FIG. 3 is a block diagram illustrating various examples of submitters and expert computing devices communicating with a crowdsourcing server of the expert opinion crowdsourcing system, according to an embodiment of the present disclosure.

FIG. 3 is a block diagram illustrating various examples of submitters and expert computing devices communicating with crowdsourcing server 100, according to an embodiment of the present disclosure. In certain figures herein, blocks may be labeled with an indicator of an individual or person that may control a computing device, such as a submitter or an expert. Each such block may also include a computing system or device, such as one of the computing systems or devices illustrated with reference to FIG. 2A (for example, case submitter computing device 110 and/or expert reader computing device 120). Similarly, certain figures may be labeled with indicators of computing systems or devices, rather than individuals or persons that operate the computing systems. Reference herein to an individual (such as a submitter or expert) or a computing system or device (such as a case submitter computing device or expert reader computing device) may refer to either the individual (for example, a submitter or expert) and/or the computing system utilized by the individual (for example, the computing device used by the submitter or the computing system used by the expert).

As shown in the example of FIG. 3, multiple submitter computing devices 310 (including 310a, 310b, 310c, 310d, 310e, and 310f) may be in communication with the crowdsourcing server 100 via the network 150. As shown, the submitters may comprise various individuals that may submit medical cases to the crowdsourcing server 100 for a variety of purposes and desired feedback options. For example, submitter 310f may be a patient that may be submitting his/her own medical images in order to get an opinion or reading (or second, third, or fourth, among others) of a radiology exam. In an embodiment, the patient may be submitting an exam that has already been read, for example, for another opinion. In another embodiment, the patient may be submitting an exam that has not been previously read to obtain one or more readings of their medical imaging exam.

Submitter 310e may comprise, for example, a third-party, such as an insurance company, law firm, or the like. The third-party may request, for example, one or more expert reports on a medical case of a client (or adverse party) in order to prove or disprove an insurance claim or legal case. Submitter 310a may comprise, for example, a referring doctor who may be requesting expert reports regarding a patient's case for various purposes. For example, the referring doctor may be requesting reports to provide a further comfort level and/or guidance in a determined treatment course, and/or at the request of a patient. Submitter 310b may comprise, for example, a radiologist that may be unsure of a particular diagnosis and who may desire other opinions in order to increase the likelihood that the radiologist's final report is accurate. These are just example motivations and purposes for providing medical data to the crowdsourcing server 100; any other entity may be a submitter and may submit medical data (or other types of data) for any other purpose (although, as discussed herein, rules and/or characteristics established by experts and/or the crowdsourcing server may limit which medical data is actually reviewed by particular experts).

As shown in FIG. 3, and according to an embodiment, the system may include expert computing devices 320a and 320b. The expert computing devices 320a and 320b may be operated by experts, as determined by the crowdsourcing server 100 and/or other entity. For example, the experts that control computing devices 320a and 320b may be radiologists, or people in training, that may desire further skill tuning that may be achieved by reviewing more difficult cases that may be available through the crowdsourcing server 100.

Additional Example Methods

Figure 4:
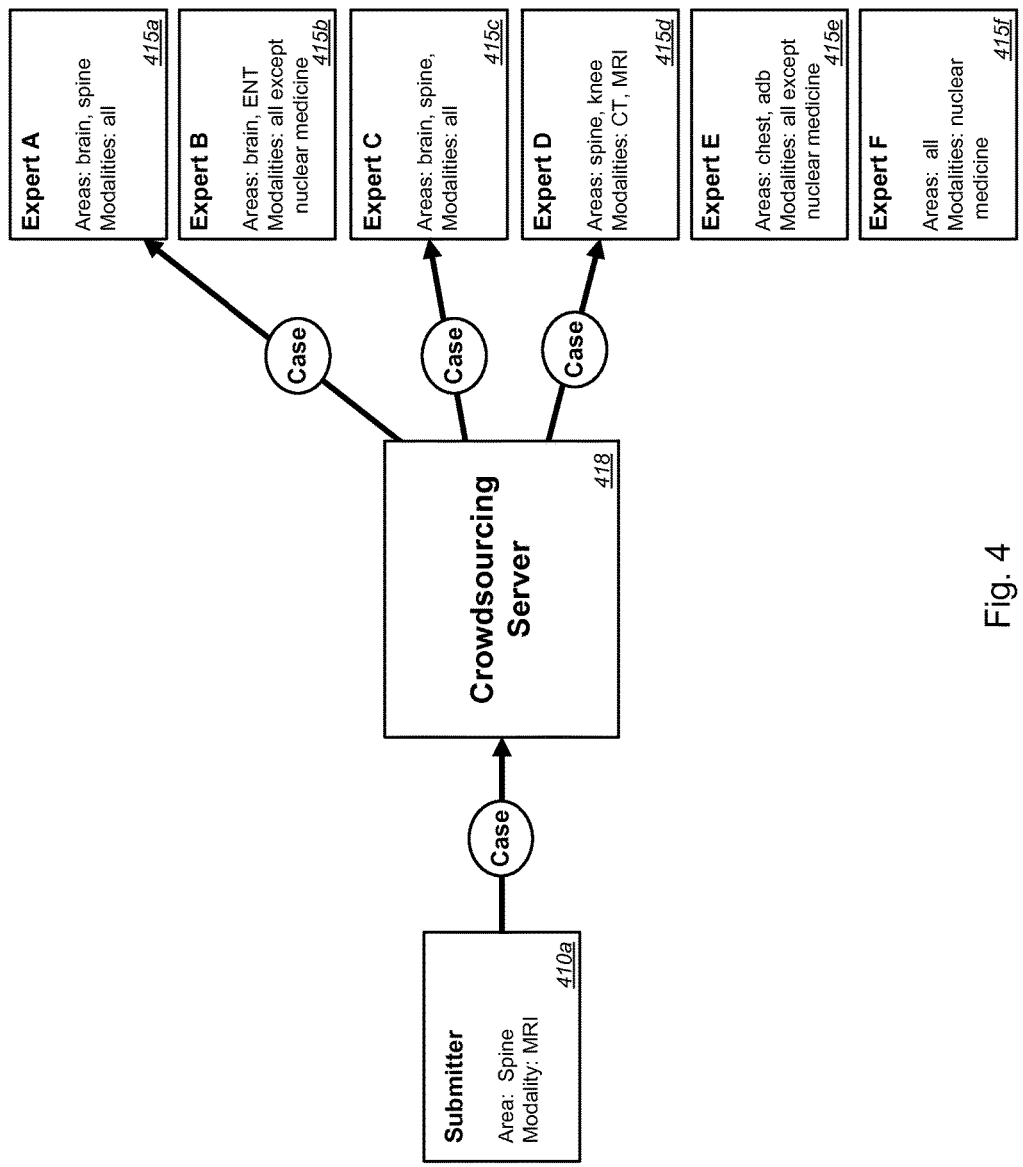
FIGS. 4-8 are flow diagrams illustrating example methods or processes of the expert opinion crowdsourcing system in which cases from submitters are provided to experts, according to embodiments of the present disclosure.

FIGS. 4-8 are flow diagrams illustrating example methods or processes of the expert opinion crowdsourcing system in which cases from submitters are provided to experts, according to embodiments of the present disclosure. Turning to FIG. 4, the flow diagram illustrates an example flow of a medical case from a submitter 410a, to a crowdsourcing server 418, and then on to some of multiple experts 415a-415f. The example of FIG. 4 illustrates several aspects of the system including, for example:

Cases may be associated with characteristics. In the example illustrated, cases may be associated with a region or area of a body imaged (in this example the spine) and the medical imaging modality utilized (in this example, MRI). As described above, characteristics, a complexity, and/or other information related to a case may be provided by a submitter and/or determined from case data automatically (for example, from metadata associated with the case).

Experts may be associated with areas of expertise that correlate with exam characteristics. In various embodiments, areas of expertise of experts may be determined in a variety of ways including, for example: by the experts themselves (for example, the expert may provide information regarding their expertise), by ratings of experts by others (for example, a credentialing panel, other experts, feedback from submitters, and/or the like), by testing the expert, by the expert's training, by a specialty board associated with the expert, and/or by a license associated with the expert, among others.

As mentioned above, various characteristics, or expertise, may be associated with experts including, for example, characteristics of cases the experts are willing to accept, areas and/or modalities they are willing to accept, and the like. In various embodiments, these characteristics and others may be stored in one or more databases of the system.

The crowdsourcing server 418 may be configured to automatically communicate cases where the characteristics of a case match the characteristics, such as expertise, of the expert.

In the example of FIG. 4, a Spine MRI case is submitted by a submitter 410*a*, the case is determined to be compatible with particular experts based on the experts' characteristics, and the case is communicated to (or made available to) Experts A, C, and D as their areas of expertise match the characteristics of the submitted exam.

As described above, characteristics, a complexity, and/or other information associated with a case may be determined automatically by the system. In an embodiment, the system may automatically determine characteristics associated with a medical exam from a DICOM header file, DICOM metafile, and/or other metadata or data included in the medical exam and/or electronic medical record. For example, a DICOM modality of a medical image or an image series may be automatically detected and/or determined from a DICOM metafile associated with the medical image or image series. In another example, for a medial image, an anatomical area of interest may be determined from a DICOM header and/or an Exam Description (or other item of information) associated with the medical image. An Exam Description (or other item of information) may be a coded value (for example, a CPT-code (Current Procedural Terminology code) or SNOMED CT code) or non-coded value. In yet another example, a patient may submit a report to the system (such as an imaging examination clinical report, surgical report, or other expert report) for a crowd-sourced review, and the system may assess various codes associated with the report and/or text within or associated with the report to determine characteristics of the report. In an embodiment, the system may use natural language processing to extract case characteristics from a report.

Automatically extracted and/or determined characteristics and/or complexity of a submitted exam may be used by the system in determining particular matching experts (as described above and below). Automatic determination of case characteristics may advantageously enable an unsophisticated patient user (or other user) to submit a case to the system and find a matching expert without manually characterizing the case. For example, a patient submitter may not know that a Brain MRI ideally should require a neuroradiologist or neurosurgeon expert, or that a Sinus MRI may ideally require a Head and Neck radiologist or ENT surgeon expert. However, by automatically extracting case characteristics from a submitted case, in these examples the system may nevertheless match the exam with appropriate specialist attributes of the expert reviewer. In an embodiment, automatically extracted and/or determined characteristics may be provided to either or both of submitter(s) or expert(s) to review and/or approve (as described above in reference to FIGS. 1A and 1B). Further, a confidence regarding a correctness of automatically determined information may be determined by the system and may be reported to submitter(s) and/or expert(s).

Regarding a case complexity determination mentioned above, in an embodiment the system may automatically categorize the case or report based on level of complexity of the case or report. Determining a level of complexity may enable the system to match the case with particular experts based on subspecialty qualifications, seniority, and/or other rating systems. For example, a brain MRI may be directed to a general or neuroradiologist, while a Brain MRI with perfusion imaging and spectroscopy might be directed to a senior (or more qualified or experienced) neuroradiologist. Alternatively the system may report to both or either of the submitter or the matched expert(s) a list of candidates and the best matches based on a complexity and/or a ranking (as described above in reference to FIGS. 1A and 1B).

Figure 5:
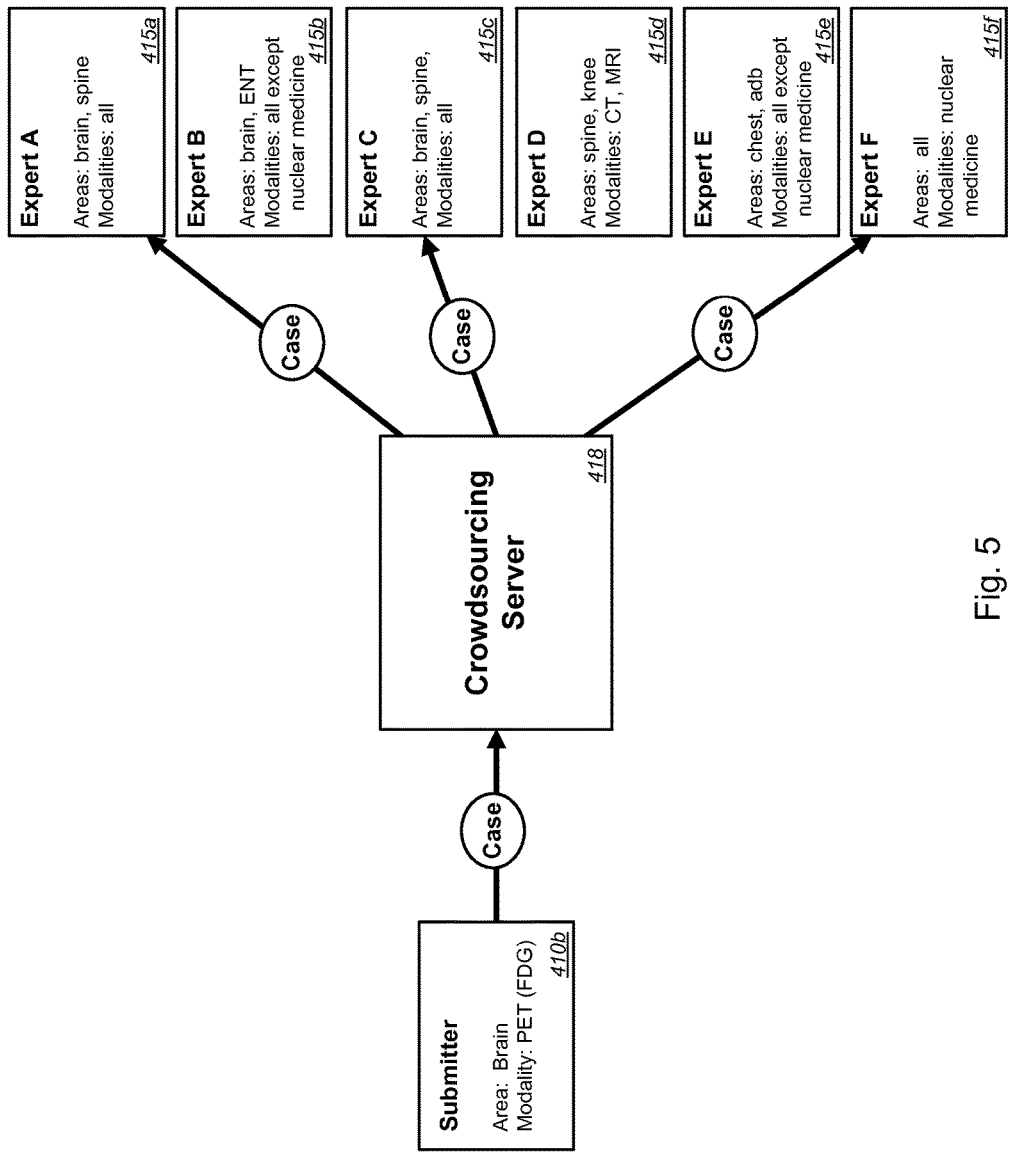

FIG. 5 is another flow diagram illustrating an example flow of a different case type: a PET of a brain. In this example, the case may be transmitted from the submitter 410*b* to the crowdsourcing server 418, and then automatically, selectively may be made available to certain experts. As shown in the illustration, the case may be communicated to, or made available to, Experts A, C, and F as their areas of expertise match the characteristics of the submitted case.

Figure 6:
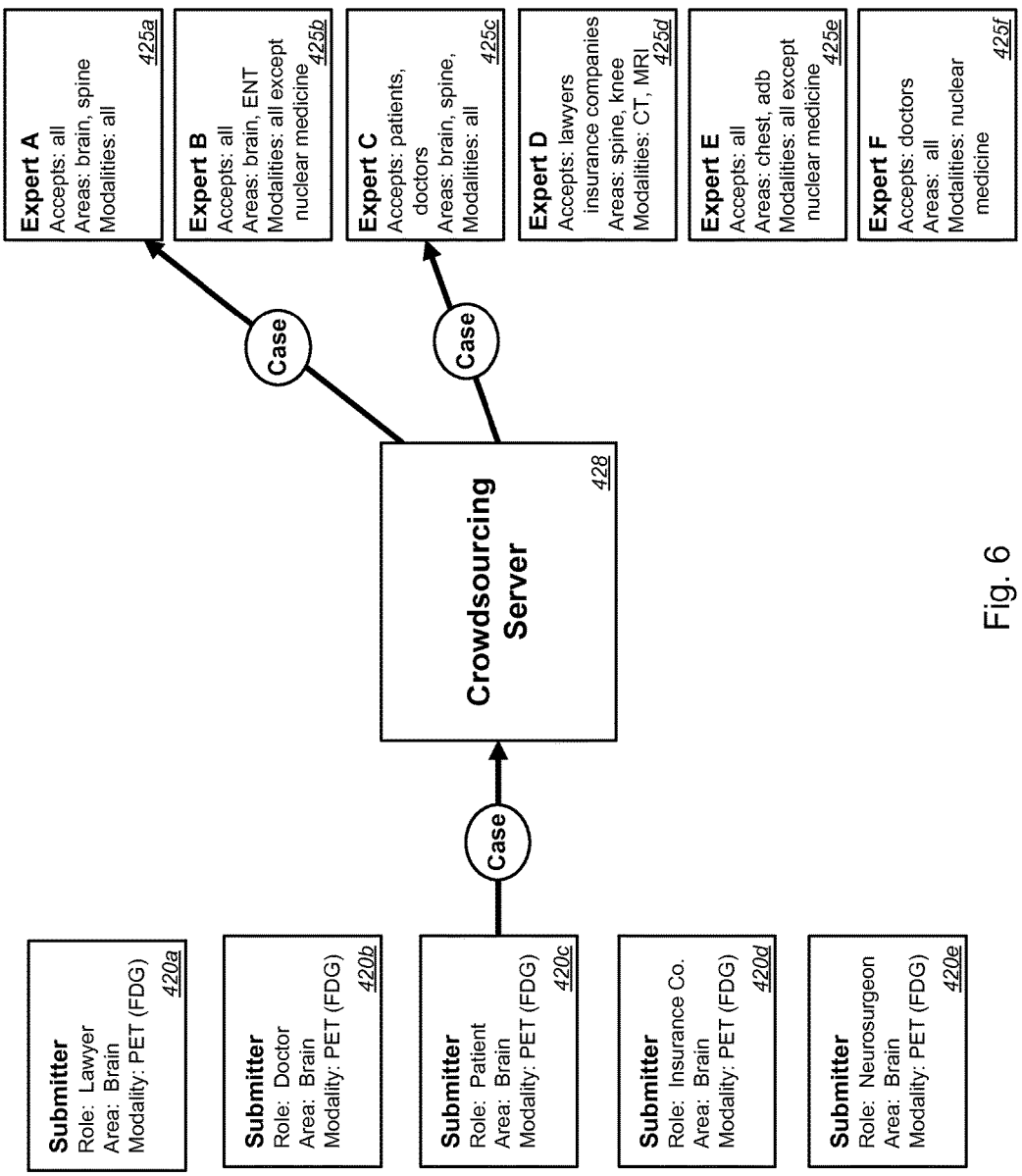

FIG. 6 is another flow diagram illustrating an example transmission of a case to a crowdsourcing server 428, and also illustrating multiple submitters 420*a*-420*e* that may each be associated with various characteristics. In the example of FIG. 6, each of the submitters is associated with a "role". For example, various roles of submitters may include lawyer, doctor, patient, insurance company, and/or neurosurgeon, among others. In other embodiments, roles may be further subdivided, for examples doctors may be further characterized by specialty, or lawyers may be further subdivided by the role the lawyer is playing with regard to a case (for example, defendant vs. plaintiff).

In the embodiment of FIG. 6, expert characteristics may include types of submitters from whom the expert is willing to accept cases. For example, the expert may specify particular submitter roles from which they accept cases. In the example illustrated, such characteristics are listed as the "Accepts" characteristic for each expert. For example, Expert A may accept cases from all types of submitters, Expert C may accept cases from patients and doctors, and Expert F may only accept cases submitted by doctors.

In the example illustrated, a patient 420*c* may submit a Brain PET to crowdsourcing server 428. The crowdsourcing server 428 may communicate the case to experts that match, both in terms of the characteristics of the case and characteristics of the submitter. For example, because the submitter 420*c* in this example is a patient that is submitting a Brain PET medical imaging exam, the exam is automatically matched to and made available to Experts A and C.

Figure 7:
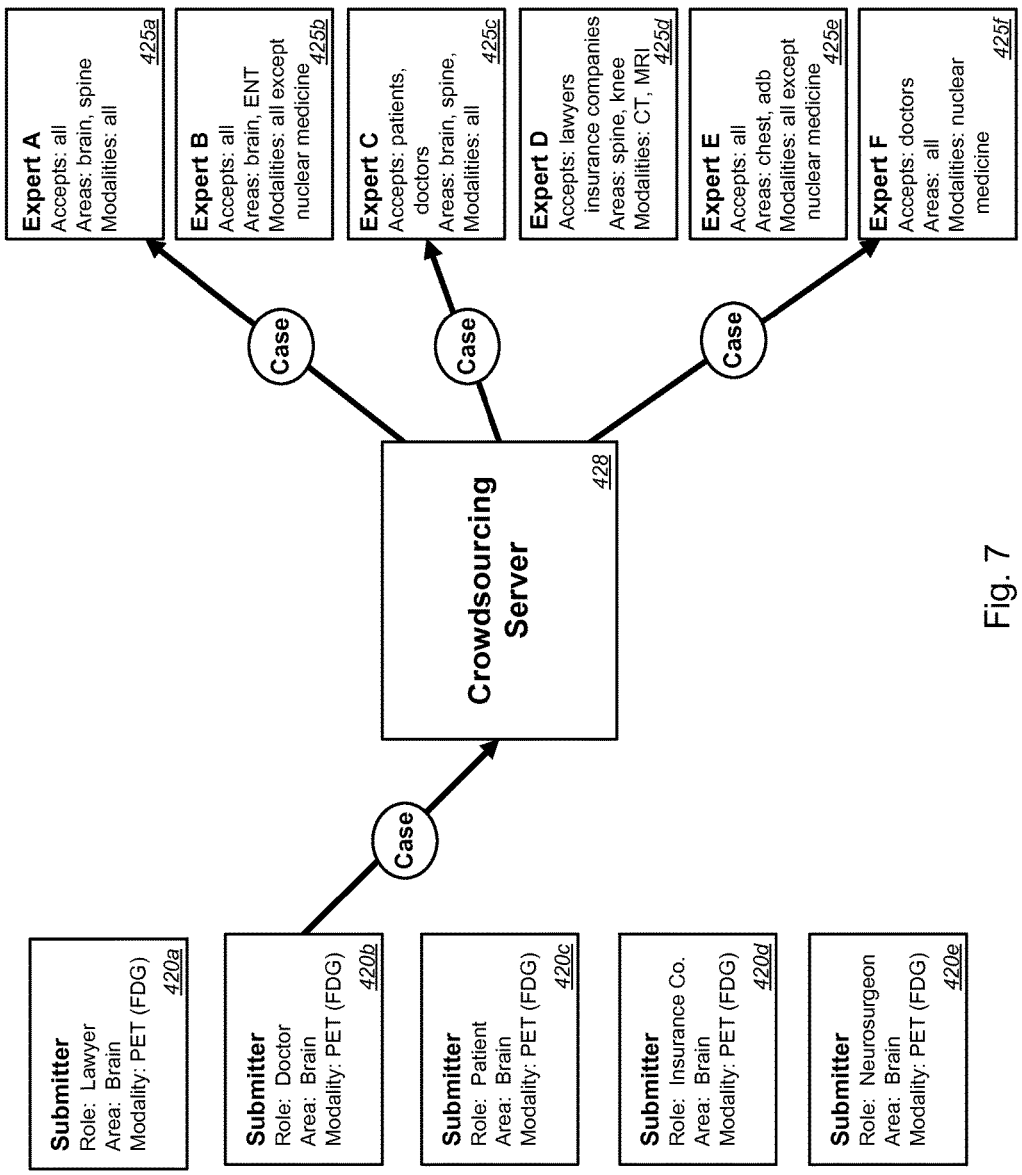

FIG. 7 is another flow diagram illustrating an example transmission of a case to the crowdsourcing server 428. In the example, the submitter 420*b* is a doctor who is submitting a case including a Brain PET. Crowdsourcing server 428 automatically communicates the case to particular experts that match, in this example Experts A, C, and F.

In other embodiments, other criteria may be used in the process of matching experts, submitters, and cases. For example, a location (such as a particular state in the USA) associated with the case may be among the criteria used to choose experts. For example, in an embodiment only experts who have a medical license in a state associated with a case may be automatically chosen. In another example, insurance may be one of the criteria used for matching submitters and experts. For example, the system may match cases to experts who are contracted with a patient's insurance company.

In another embodiment, the opposite may occur. For example, when doctors are contracted with an insurance company, the contract may prohibit them from charging the patient for a second opinion. In a case where a submitter desires to pay a doctor for a second opinion and the doctor agrees, the system may automatically match the case with experts who are NOT contracted with the patient's insurance company.

Figure 8:
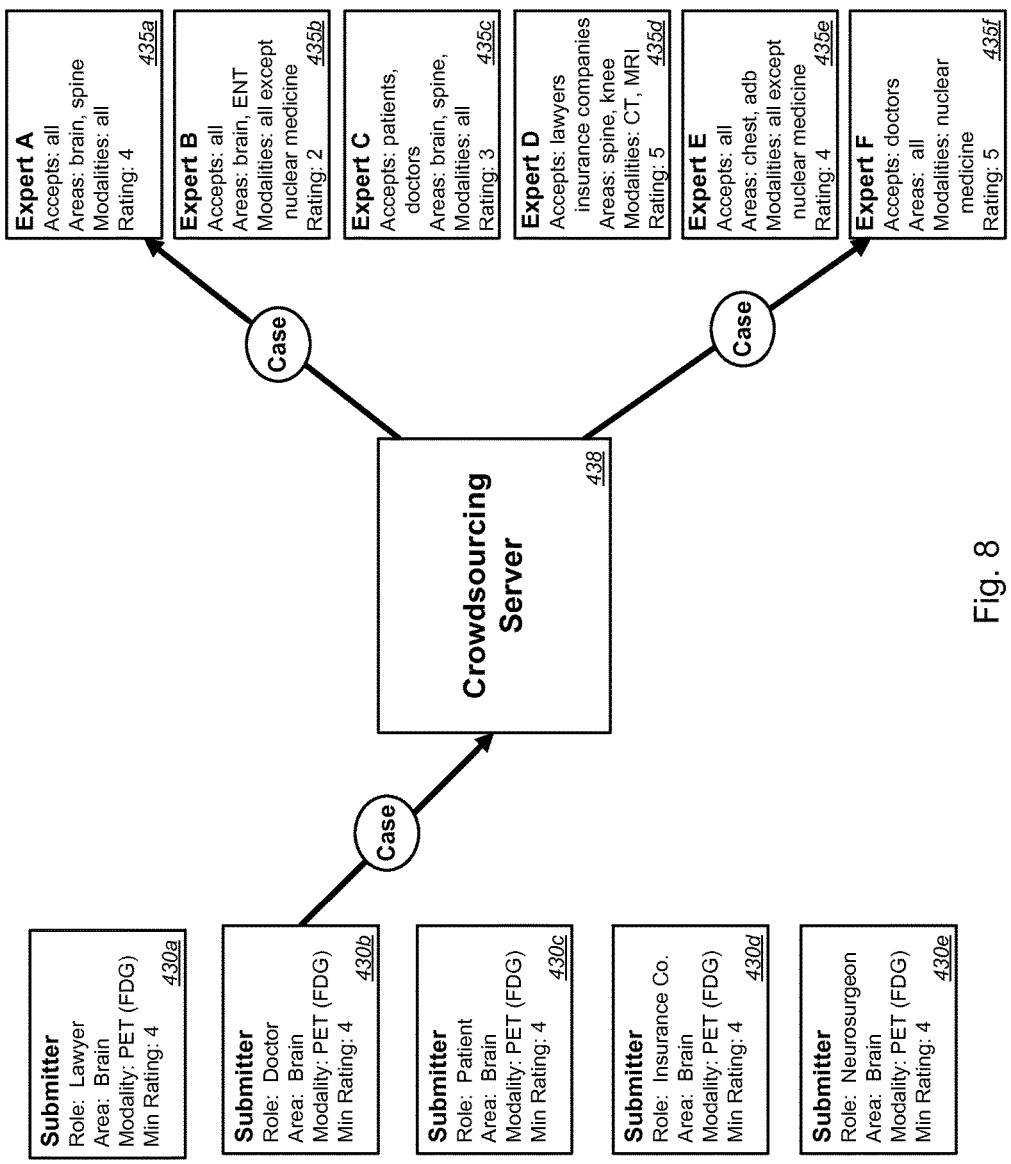

FIG. 8 is another flow diagram illustrating an example transmission of a case to a crowdsourcing servicer 438, and also illustrating association of ratings with experts (as shown in 435a-435f), and minimum rating requirements provided by submitters (as shown in 430a-430e). For example, as mentioned above, submitters may provide criteria including a particular expert rating, or minimum expert rating, when submitting a case. Expert ratings may be generated and/or updated by the system based on a variety of factors including, for example:

Ratings provided by submitters (for example, after having received a report from an expert).
Ratings provided by specific types of submitters (for example, patients, other experts, or the like).
Ratings provided by a credentialing panel.
Ratings provided by other experts.
An expert's performance on a test or multiple tests.
An expert's level of training and/or experience.
A certification by, for example, a licensing board, a specialty board, and/or the like.

In various embodiments, when an expert and/or expert report is rated and/or feedback is provided by others, the system may weigh the rating based on attributes of the person providing the rating. For example, the system may determine an overall rating that takes into account the attributes of particular rating providers by, for example, placing a greater weight on a rating provided by a more qualified person or expert. In an embodiment, the system may disclose the characteristics or attributes of specific persons providing ratings to, for example, submitters of a case. For example, a submitter may provide a case that may be matched with an expert. In reviewing the expert information prior to making a determination to send the case to the expert, the submitter may view not just a rating of the expert, but a breakdown of ratings of the expert, for example, "This expert is rated an 8/10 by general radiologists, and a 6/10 by neuroradiologists." Similarly, ratings for specific report may be provided by the system.

In the embodiment of FIG. 8, each of the experts 435a-435f is associated with a rating. In one embodiment, submitters may indicate a minimum rating of experts who may receive the case being submitted. Further, in an embodiment a submitter may indicate a particular number of experts to review the case. For example, a submitter may indicate a minimum rating of 4, and 1 expert report, for a particular case. The system (for example, the crowdsourcing server 438) may determine that two experts match the characteristics provided with the case. In this example, the system may automatically provide the case to the expert having the highest rating.

In the example illustrated in FIG. 8, a submitter that is a doctor may submit a case that is a Brain PET, and may indicate that any experts that receive the case must have a minimum rating of 4. As shown in the example, the case may be communicated to Experts A and F, as those experts match in terms of the types of submitter from whom the expert will accept cases, the characteristics of the exam, and the minimum rating of the expert that is acceptable to the submitter.

In various embodiments, any type of rating scale may be used by the system. For example, a rating scale may range from 1-5 (with either 1 or 5 being the best), or 1-10 (with either 1 or 10 being the best), just to name two examples. Further, multiple ratings may be associated with each expert. For example, an expert may be associated with one rating that may be relevant to a particular type of submitter (for example, patient submitters) and another rating that may be relevant to a different particular type of submitter (for example, doctor submitters). In another example, an expert may be associated with one rating relevant to one area of expertise, such as imaging of the brain, and another rating relevant to another area of expertise, such as imaging of the chest.

FIGS. 9-10 and 11A-11B are flow diagrams illustrating example methods or processes of the expert opinion crowdsourcing system in which cases from submitters are provided to experts, and reports from experts are provided to submitters, according to embodiments of the present disclosure.

Figure 9:
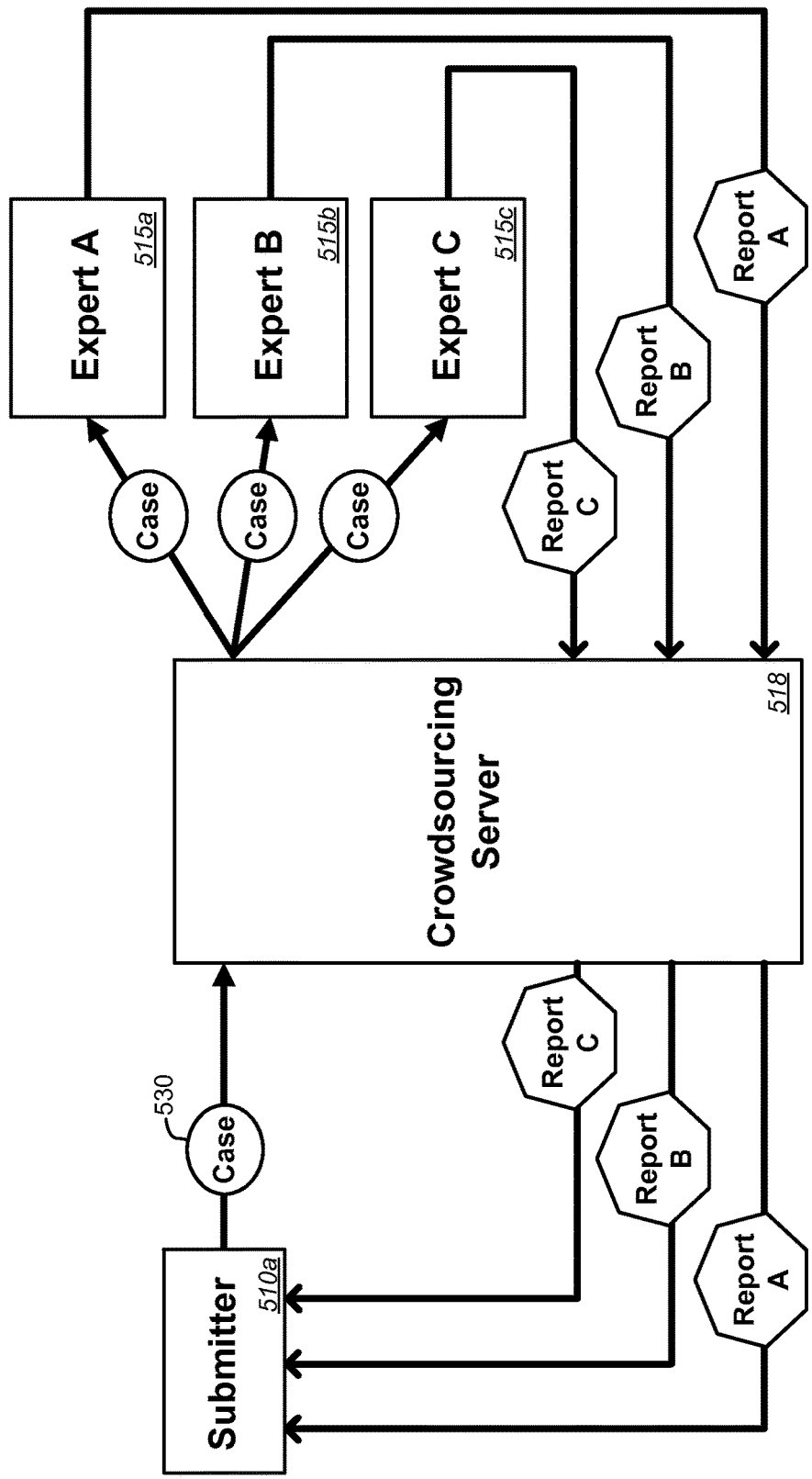
FIGS. 9-10 and 11A-11B are flow diagrams illustrating example methods or processes of the expert opinion crowdsourcing system in which cases from submitters are provided to experts, and reports from experts are provided to submitters, according to embodiments of the present disclosure.

Turning to FIG. 9, a flow diagram is shown illustrating an example overview of communications starting from transmission of a case by a submitter to a crowdsourcing server, and finishing with the submitter receiving reports from multiple experts. In the embodiment of FIG. 9, a submitter 510a may submit a case 530 to the crowdsourcing server 518 and the case may be communicated to a number of experts 515a, 515b, and 515c. The determination to transmit the case to Experts A, B, and C may be based on the functionality described above. In addition to the functionality described above, other criteria may be used to automatically determine how cases are communicated to experts. For example, a submitter may indicate a maximum number of experts to which a case is to be communicated, and/or may indicate a desire to have the case evaluated by multiple experts.

As shown in the embodiment of FIG. 9, experts 515a, 515b, and 515c, each provide reports back to the crowdsourcing server 518, which may then automatically communicate the reports to the submitter 510a or make the reports available to the submitter 510a. In some embodiments, the experts 515a-515c may communicate the reports directly to the submitter 510a.

Figure 10:
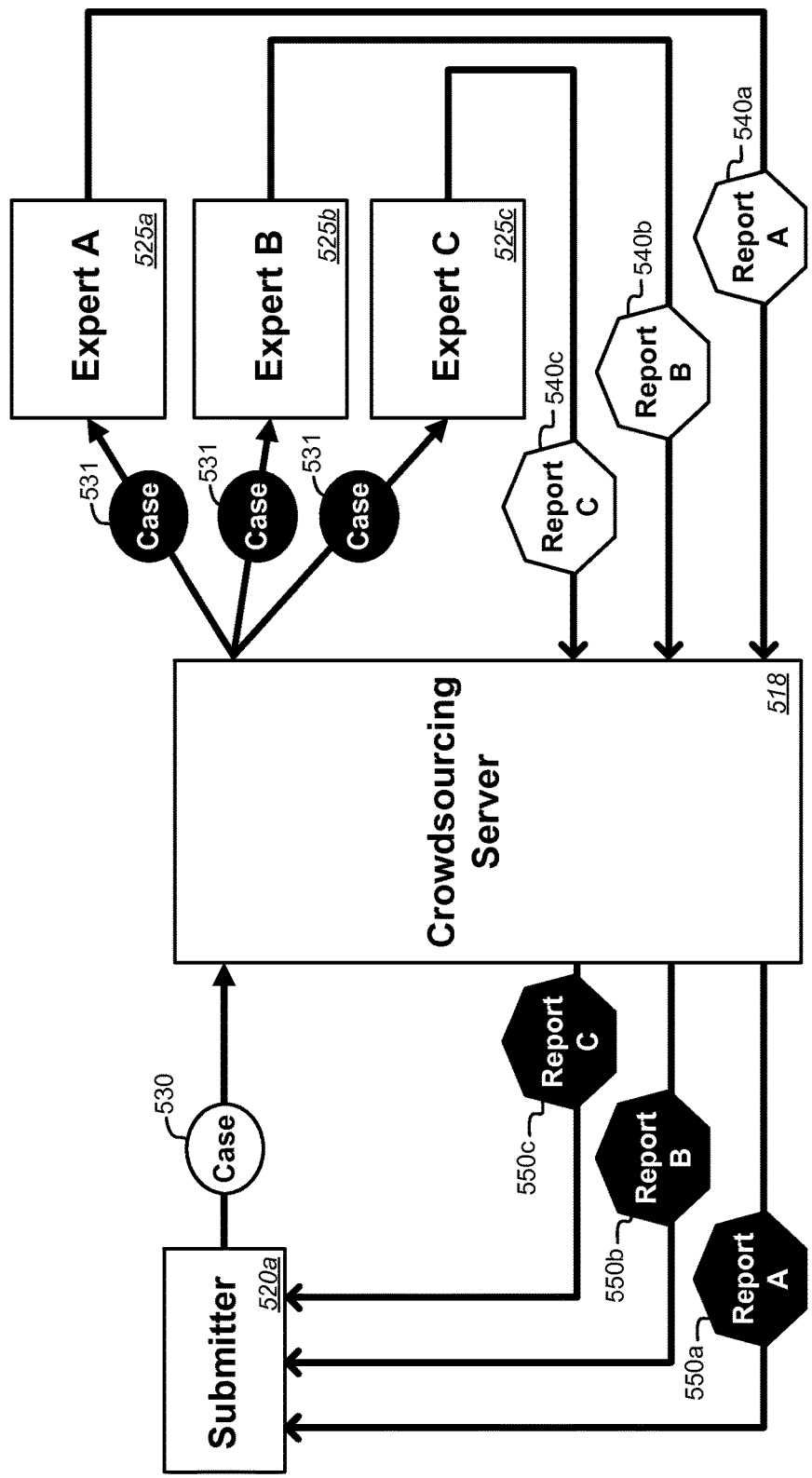

FIG. 10 illustrates an example including components similar to those of FIG. 9. In the example of FIG. 10, however, the case 530 submitted by the submitter 520a, as well as the reports provided by experts 525a-525c, are anonymized by the crowdsourcing server 518. In some embodiments, cases may be anonymized, for example such that experts may be unaware of an identity of a submitter and/or a patient associated with a case. Similarly, in some embodiments, reports may by anonymized such that, for example, a submitter and/or patient associated with a case may be unaware of an identity of an expert.

In some embodiments, the crowdsourcing server may track information that may allow the identity of the case, expert, and/or submitter to be determined. For example, a patient submitter may submit a case and indicate that it is to be anonymized. In addition, an expert may require that a report be anonymized so that the patient and/or submitter associated with the report are not identified. In another example, the identity of the expert creating the report may be hidden.

After the submitter receives a report, the submitter may request the identity of an expert so that the submitter may communicate further. If the expert agrees to be identified to the patient, and the patient agrees to be identified to the expert, then the crowdsourcing server 518 may provide the identifying information to each party and/or provide functionality that may allow the two parties to communicate (for example, to create a doctor-patient relationship).

In an embodiment, an expert may provide criteria that may require that cases that they accept include contact information for a physician caring for a patient associated with a submitted case so that the expert may contact the patient's physician if the expert finds a significant abnormality.

Figure 11A:
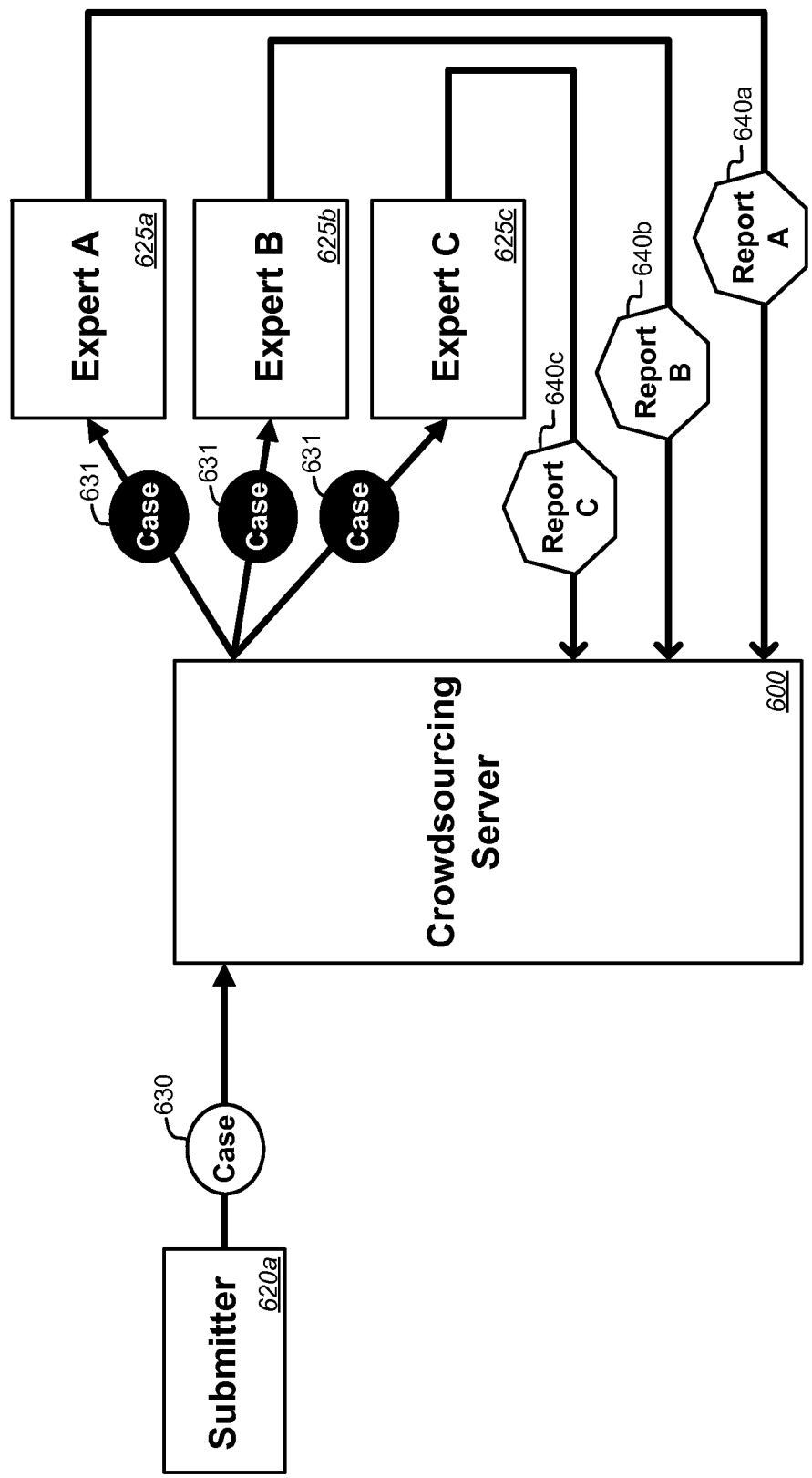
Figure 11B:
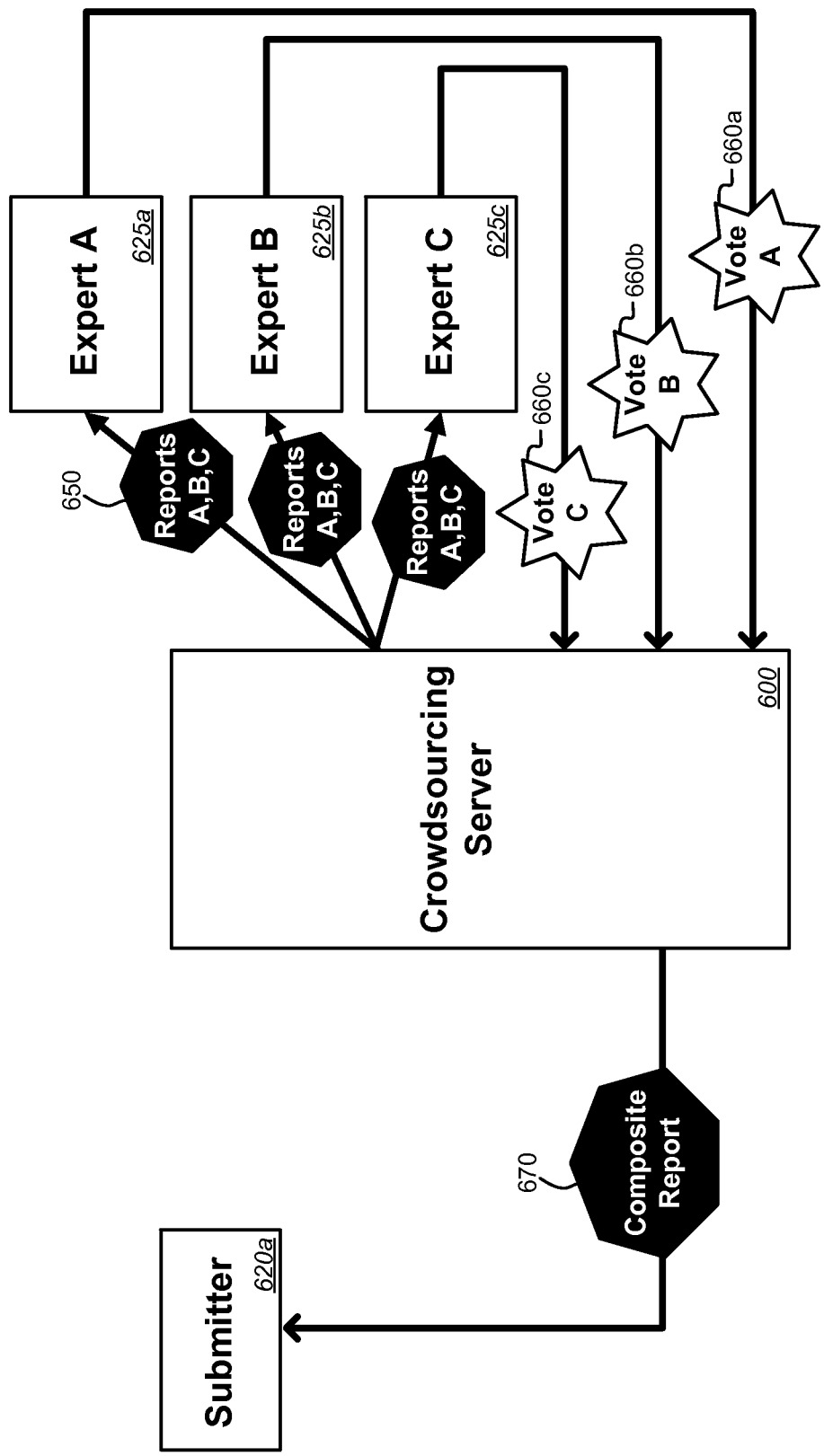

As mentioned above, FIGS. 11A and 11B are sequential flow diagrams showing an example method of the expert opinion crowdsourcing system, according to an embodiment. FIGS. 11A and 11B show an example method that may allow for rating of reports of experts. In an embodiment, rating of expert report may, for example, put various experts in a sort of competition to provide the best and/or most accurate reports. FIG. 11A demonstrates initial steps in the embodiment, and FIG. 11B demonstrates additional steps. As in some other embodiments, submitters and experts may indicate criteria that may be used to determine how a crowdsourcing server 600 automatically matches experts, submitters, and cases.

In the example of FIG. 11A, a submitter 620a may communicates a case 630 to the crowdsourcing server 600. As described in other embodiments, the crowdsourcing server 600 may automatically choose one or more experts to which the case is to be communicated.

In this embodiment, the case is then anonymized by the crowdsourcing server 600, and then the anonymized case 631 is communicated to matching experts 625a, 625b, and 625c. Depending on the embodiment, anonymization may take different forms. For example, in one embodiment, anonymization may comprise removing any personally identifiable information from the case 630, such as a patient's name, contact information, and/or the like. In some embodiments, anonymization may include removing such data from actual medical images, for example, medical images that have personally identifiable information included in the images. In some embodiments, the crowdsourcing server 600 may include image analysis capabilities that allow automatic identification and obfuscating (or removal) of personal information of a patient. In some embodiments, anonymization may further comprise removal of information regarding a source of the images (for example, an imaging center), information regarding a referring doctor that originally requested the medical images, information regarding a location of a patient, doctor, and/or imaging center, and/or any other information. In another embodiment, the case may not be anonymized.

In an embodiment, the each of the experts 625a-625c may be notified of the experts 625a-625c that have been matched to the particular case 630. In other embodiments, each of the experts may have no knowledge of other experts that have been matched to a particular case.

In the example of FIG. 11A, experts 625a, 625b and 625c, create reports 640a, 640b, and 640c, which may be communicated to the crowdsourcing server 600. In some embodiments, the crowdsourcing server 600 may provide a graphic user interface that experts may use to create reports directly on the crowdsourcing server 600.

Continuing on to FIG. 11B, the reports from various experts may be anonymized and communicated to one or more "feedback entities," such as experts (e.g., experts that provided reports and/or other experts), the submitter, and/or any other entity from which feedback on reports may be desired (e.g., individuals that are neither the submitter nor an expert that provides a report), for evaluation and/or feedback. For example, a compilation of reports received from multiple experts may be provided to one or more experts, wherein a source of individual reports may not be identifiable. In the example of FIG. 11B, a compiled report 650, which may include reports from each of the experts 625a, 625b, and 625c, may be communicated from the crowdsourcing server 600 to each of the experts. The compiled report 650 may simply include each of the expert reports in their entireties, or may include portions of the reports, such as in a table or chart format configured for easier review of the multiple reports. In other embodiments, the reports may not be anonymized before being communicated to the experts.

In another embodiment, the group of experts receiving the reports may be different than the experts that created the reports. For example, in one embodiment radiologists without specialized training in neuroradiology may view neuroradiology cases and provide reports, while a group of experts evaluating (and/or providing feedback on) the reports may be restricted to neuroradiologists (for example, radiologists with subspecialty training in neuroradiology).

In another embodiment, the group of experts evaluating the reports may include one or more of the group of experts that created the report as well as one or more other experts.

In yet another embodiment, the people rating and/or providing feedback on the reports may not be experts. For example, in one embodiment people who are not physicians may provide feedback concerning and/or rate medical reports based on how clearly each expert's reports communicated their opinions to people without medical training. In another embodiment, submitters may provide feedback concerning and/or rate the experts' reports.

The group evaluating the reports may then vote, applying a rating to each of the reports. For example, in one embodiment each of the voting experts (the experts that have access to reports provided by other experts for the purpose of providing feedback on the reports) votes for the report or diagnosis that they think provides the most accurate evaluation of the case. In other embodiments, other feedback and/or voting processes may be performed by the voting experts. The votes (660a, 660b, and 660c) from the experts may be communicated to the crowdsourcing server 600. In an embodiment, the crowdsourcing server 600 may provide a user interface that may allow the experts evaluating the reports to view the case and vote on the reports, for example via a web browser interface.

Based on the votes 660a-660c received by the crowdsourcing server 600, experts may receive points based on the ratings of their report. These points may be used to determine a "best" (or "winner") report or diagnosis which may be made available to the submitter. Such points may be used to determine and/or update an expert's rating and/or raking, such as with reference to a particular specialty associated with the case and/or an overall rating for the expert. In an embodiment, this rating and/or ranking may be made available to others, such as submitters, who may use it as a criterion for selection of experts, for example for additional case submissions.

In an embodiment, the crowdsourcing server 600 may generate a composite report 670 with may include results of the voting and/or the various reports generated by the experts 625a-625c. For example, the composite report 670 may include each of the individual reports listed in an order based on the voting. In another example, the composite report 670 may include portions of each of the reports based on the voting.

Additional Embodiments

In an embodiment, the crowdsourcing server may post (for example, on a website) a request and/or challenge for medical data that may be useful to others. For example, the expert opinion crowdsourcing system may collect pathologically proven cases that have been reviewed by one or more experts. In another example, the crowdsourcing server may post a challenge, such as "In the next 60 days, we want to build a file of the most common imaging findings a first year resident should know how to recognize before they start taking call," in order to obtain data from a vast audience of experts that may be useful for a particular purpose (for example, educating medical trainees in this example).

In another embodiment, the expert opinion crowdsourcing system includes a publicly accessible user interface (generated by, for example, a software module of the crowdsourcing server) that may include, for example, ratings associated with experts.

In an embodiment, experts receiving positive feedback or ratings from, for example, submitters, other experts, and/or other feedback entities, may receive rewards. For example, an expert receiving a highest rating from among a group of experts reviewing/providing a report on a case may receive an award. Examples of reward may include monetary rewards, notations, badges, discounts, notoriety, and/or the like. Such rewards may be included on (or in), for example, a user interface of the system.

Example Computing System Components and Operation

As described above, FIG. 2A illustrates various components of a crowdsourcing server 100, a case submitter computing device 110, and an expert reader computing device 120. Each of these computing systems or device may, in various embodiments, take various forms. For example, each of the computing systems or devices may include any combination of the components and/or functionality described below, as well as other computer hardware and/or software. The hardware will be discussed with reference to a "computing system," which could apply to any of the crowdsourcing server 100, the case submitter computing device 110, and/or the expert reader computing device 120.

In one embodiment, the computing system may be a computer workstation having one or more software modules (for example, modules 101, 111, 121). In other embodiments, software modules may reside on other computing devices, such as a web server or other server, and the user directly interacts with a second computing device that is connected to the web server via a computer network.

In one embodiment, the computing system comprises a server, a desktop computer, a workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing system may run an off-the-shelf operating system such as Windows, Linux, MacOS, Android, or iOS. The computing system may also run a more specialized operating system which may be designed for the specific tasks performed by the computing system.

The computing system may include one or more computing processors (for example, processors 181, 181a, and 181b). The computer processors may include central processing units (CPUs), and may further include dedicated processors such as graphics processor chips, or other specialized processors. The processors generally may be used to execute computer instructions based on the software modules to cause the computing device to perform operations as specified by the modules. The modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, Lua, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The computing system may also include memory (for example, RAM/storage 182, 182a, and 182b). The memory may include volatile data storage such as RAM or SDRAM. The memory may also include more permanent forms of storage such as a hard disk drive, a flash disk, flash memory, a solid state drive, or some other type of non-volatile storage.

The computing system may also include or be interfaced to one or more peripheral devices or input/output devices (for example, input/output devices 183, 183a, and 183b) that provide and/or receive information to/from the users. Peripheral devices may include one or more display devices that may include a video display, such as one or more high-resolution computer monitors, or a display device integrated into or attached to a laptop computer, handheld computer, smartphone, computer tablet device, or medical scanner. In other embodiments, the display device may include an LCD, OLED, or other thin screen display surface, a monitor, television, projector, a display integrated into wearable glasses, or any other device that visually depicts user interfaces and data to viewers.

The peripheral devices may also include or be interfaced to one or more input devices which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The computing system may also include one or more interfaces which allow information exchange between computing system and other computers and input/output devices using systems such as Ethernet, Wi-Fi, Bluetooth, as well as other wired and wireless data communications techniques.

The modules of the computing system may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of the computing system may be combined into fewer components and modules or further separated into additional components and modules.

The computing system may communicate and/or interface with other systems and/or devices. In one or more embodiments, the computer system may be connected to a computer network 150. The computer network 150 may take various forms. It may be a wired network or a wireless network, or it may be some combination of both. The computer network 150 may be a single computer network, or it may be a combination or collection of different networks and network protocols. For example, the computer network 150 may include one or more local area networks (LAN), wide area networks (WAN), personal area networks (PAN), cellular or data networks, and/or the Internet.

Depending on the embodiment, certain acts, events, or functions of any of the processes or algorithms described herein may be performed in a different sequence, may be added, may be merged, and/or may be left out altogether (for example, not all described operations or events are necessary for the practice of the process or algorithm). Moreover, in certain embodiments, operations or events may be performed concurrently, for example, through multi-threaded processing, interrupt processing, or multiple processors or processor cores or on other parallel architectures, rather than sequentially.

The various illustrative logical blocks, modules, routines, and algorithm steps described in connection with the embodiments disclosed herein may be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The steps of a method, process, routine, or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of a non-transitory computer-readable storage medium. An example storage medium may be coupled to the processor such that the processor may read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y, and at least one of Z to each be present.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computer-implemented method comprising:
    under direction of one or more hardware processors configured with specific software instructions,
    receiving a medical image series including one or more medical images;
    providing a user interface to a user, the user interface configured to allow the user to set preferences for selection of one or more reviewers of the medical image series, the preferences including:
        first preferences identifying a first medical specialty and a first minimum quantity of reviewers having the first medical specialty;
        second preferences identifying a second medical specialty and a second minimum quantity of reviewers having the second medical specialty; and
        third preferences indicating a criteria regarding one or more of:
            whether reviewers offer availability to be contacted directly by the user;
            whether reviewers offer availability to review the medical image series as part of at least one of: a legal investigation, an insurance investigation, a consultation with a doctor, or a request of a patient;
            a minimum and/or maximum quantity of reviewers to be selected to review the medical image series;
            a minimum and/or maximum quantity of reviewers permitted to provide review information; and/or
            a minimum average user feedback required for reviewers to be selected for review of the medical image series;

receiving, via the internet, the preferences provided by the user;

automatically analyzing the medical image series, at least in part based on natural language processing, to determine one or more characteristics of the medical image series;

accessing a reviewer database storing a plurality of reviewer records associated with a corresponding plurality of reviewers, each of the reviewer records indicating one or more characteristics of the corresponding reviewer;

comparing the preferences set by the user and the one or more characteristics of the medical image series to respective reviewer records in the reviewer database;

selecting, based on said comparison of the first preferences and the one or more characteristics of the medical image series to respective reviewer records, a first subset of reviewers including at least the first quantity of reviewers each having the first medical specialty;

selecting, based on said comparison of the second preferences and the one or more characteristics of the medical image series to respective reviewer records, a second subset of reviewers including at least the second quantity of reviewers each having the second medical specialty;

selecting, based on said comparison of the third preferences and the one or more characteristics of the medical image series to respective reviewer records, a third subset of reviewers including one or more reviewers having characteristics matching the third preferences;

automatically analyzing the medical image series to identify personally identifiable information in the medical image series;

automatically anonymizing the medical image series by removing or obscuring the personally identifiable information from the medical image series;

providing a notice, via a computerized user interface, to the selected first, second, and third subsets of reviewers indicating availability of the medical image series for review, the medical image series having been anonymized, wherein an identity of the user is also anonymized such that the first, second, and third subsets of reviewers cannot determine the identity of the user from the notice indicating availability of the medical image series or from the medical image series;

receiving separate medical reports from each reviewer of the first, second, and third subsets of reviewers;

anonymizing identities of each reviewer of the first, second, and third subsets of reviewers such that receivers of the medical reports cannot determine the identities of the reviewers of the first, second, and third subsets of reviewers from the medical reports;

providing, via a computerized user interface, the medical reports to a plurality of rating entities, the medical reports having been anonymized;

receiving, via a computerized user interface, from each of the rating entities, a separate rating for each of the medical reports, the ratings indicating accuracy of respective medical reports;

for each reviewer of the first, second, and third subsets:
compiling ratings of the reviewer from the plurality of rating entities; and
determining an overall rating of the reviewer;

generating a composite report comprising information on each of the medical reports from the first, second, and third subsets of reviewers, wherein the composite report indicates one of the medical reports associated with a highest overall rating and include one of:
the medical reports from each of the first, second, and third subsets of reviewers, the medical reports having been anonymized; or
summaries of at least some of the medical reports from the first, second, or third subsets of reviewers, the medical reports having been anonymized;

providing the composite report to the user;

receiving a request from the user to contact a first reviewer associated with a first medical report, the first medical report having been anonymized;

automatically determining an identity of the first reviewer;

requesting authorization from the first reviewer to provide the identity of the first reviewer to the user; and in response to receiving authorization from the first reviewer to provide the identity of the first reviewer to the user, providing the identity of the first reviewer to the user.

2. The computer-implemented method of claim 1 further comprising:
providing the composite report to each at least some of the rating entities.

3. The computer-implemented method of claim 2, wherein the rating entities include one or more of the patient, one or more of the determined reviewers, and/or other reviewers that did not provide review information.

4. The computer-implemented method of claim 2, wherein the rating entities include reviewers that did not provide medical reports, but that have an expertise with reference to a medical field associated with the one or more medical images.

5. The computer-implemented method of claim 4, wherein one or more of the plurality of determined reviewers does not have an expertise with reference to the medical field associated with the one or more medical images.

6. The computer-implemented method of claim 2 further comprising:
providing a feedback user interface to the plurality of rating entities, the feedback user interface configured to receive votes from respective rating entities regarding which received medical report includes a most accurate assessment of the one or more medical images.

7. The computer-implemented method of claim 6 further comprising:
compiling votes from at least some of the rating entities; and
determining updates to ratings and/or user feedback associated with respective reviewers based on the compiled votes.

8. The computer-implemented method of claim 7 further comprising:
providing a public user interface that is publicly accessible and/or is accessible to a widely accessible audience and includes the updated ratings for the reviewers.

9. The computer-implemented method of claim 1 further comprising:
providing an award to one of the determined reviewers having a highest rating from the user.

10. The computer-implemented method of claim 9, wherein the award comprises money, discount, and/or notoriety on the user interface.

* * * * *